United States Patent [19]
Walker

[11] 4,321,272
[45] Mar. 23, 1982

[54] DERIVATIVES OF SUBSTITUTED N-ALKYLIMIDAZOLES

[75] Inventor: Keith A. M. Walker, Los Altos Hills, Calif.

[73] Assignee: Syntex (U.S.A.) Inc., Palo Alto, Calif.

[21] Appl. No.: 180,783

[22] Filed: Aug. 25, 1980

[51] Int. Cl.³ ............... C07D 405/06; A61K 31/415
[52] U.S. Cl. ............................. 424/273 R; 548/336
[58] Field of Search .................... 548/336; 424/273 R

[56] References Cited
U.S. PATENT DOCUMENTS
3,575,999 4/1971 Godefroi et al. .............. 548/336

Primary Examiner—Henry R. Jiles
Assistant Examiner—Robert C. Whittenbaugh
Attorney, Agent, or Firm—Annette M. Moore; Alan M. Krubiner

[57] ABSTRACT

Compounds useful as anticonvulsant agents, antifungals and antibacterials are represented by the formula

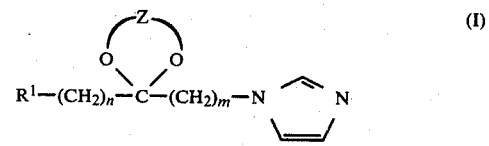

wherein $R^1$ is phenyl optionally substituted by one or more substituents selected from the group consisting of halo, lower alkyl of one to four carbon atoms, lower alkoxy of one to four carbon atoms and trifluoromethyl; Z is ethylene or propylene optionally substituted by one or more lower alkyl groups of one to four carbon atoms; m is 1, 2, 3 or 4 and n is 0, 1, 2 or 3 with the proviso that the sum of m and n is 2, 3 or 4; and the pharmaceutically acceptable acid addition salts thereof.

The ketone intermediates useful in preparing compounds of formula (I) also have anticonvulsant activity.

30 Claims, No Drawings

DERIVATIVES OF SUBSTITUTED N-ALKYLIMIDAZOLES

BACKGROUND OF THE INVENTION

1. Field of the Invention

This invention relates to cyclic ketals of N-alkylimidazoles and the pharmaceutically acceptable acid addition salts thereof which are useful as anticonvulsant agents. The invention also relates to a pharmaceutically acceptable composition containing an effective amount of at least one of the compounds in combination with a suitable excipient, the composition being useful for preventing and/or treating convulsions in mammals. The invention also relates to a process for making the compounds of the invention. The invention also relates to the pharmaceutical uses of the ketone intermediates of formula (II) used in preparing compounds of formula (I).

2. Prior Art

It is known that compounds of the formula

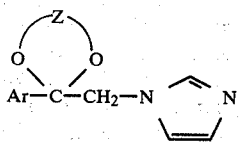

wherein Ar is inter alia phenyl, wherein the phenyl group may be substituted by one to three substituents which are independently halo, lower alkyl, lower alkoxy, nitro or cyano; and Z is —CH$_2$CH$_2$—, —CH$_2$CHR—, —CH$_2$CH$_2$CH$_2$—, or —CH(CH$_3$)—CH(CH$_3$)— wherein R is inter alia alkyl of one to ten carbon atoms exhibit antifungal and antibacterial activity. See U.S. Pat. Nos. 3,575,999 and 3,793,453, Great Britain Pat. No. 1,528,639 and Belgium Pat. Nos. 877,446 and 877,447. A novel class of compounds has now been prepared that not only exhibit antifungal and antibacterial activity but more importantly exhibit anticonvulsant activity.

SUMMARY OF THE INVENTION

The first aspect of this invention is the group of compounds represented by the formula

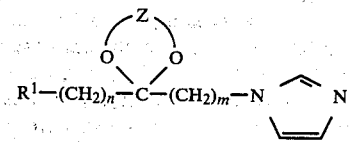

wherein
- $R^1$ is phenyl optionally substituted by one or more substituents selected from the group consisting of halo, lower alkyl of one to four carbon atoms, lower alkoxy of one to four carbon atoms and trifluoromethyl;
- Z is ethylene or propylene optionally substituted by one or more lower alkyl groups of one to four carbon atoms;
- m is 1, 2, 3 or 4 and n is 0, 1, 2 or 3 with the proviso that the sum of m and n is 2, 3 or 4; and the pharmaceutically acceptable acid addition salts thereof.

Another aspect of the invention is a method of preventing and/or treating convulsions in mammals which comprises administering an effective amount of at least one compound chosen from those represented by the above formula.

Still another aspect of the invention is a composition useful for preventing and/or treating convulsions in mammals which composition comprises an effective amount of at least one compound chosen from those represented by formula (I) above or a pharmaceutically acceptable acid addition salt thereof and a pharmaceutically suitable excipient.

Still another aspect of the invention is a process for producing a compound of formula (I) above which comprises reacting a ketone of the formula

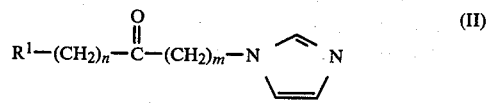

wherein $R^1$, m and n are as defined above with a suitable dihydric alcohol, or which comprises reacting a halo ketone of the formula

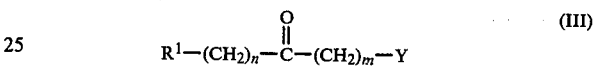

wherein $R^1$, m and n are as defined above and Y is a leaving group such as halo (chloro or bromo) or a sulfonate ester with a suitable dihydric alcohol and reacting the halo ketal formed with imidazole.

Still a further aspect of the invention is the pharmaceutical use of the ketone intermediates of formula (II).

DETAILED DESCRIPTION AND PREFERRED EMBODIMENTS

The broadest aspect of the present invention is the group of compounds represented by the formula

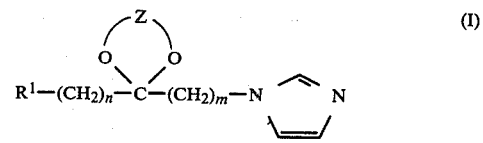

wherein
- $R^1$ is phenyl optionally substituted by one or more substituents selected from the group consisting of halo, lower alkyl, lower alkoxy and trifluoromethyl;
- Z is ethylene or propylene optionally substituted by one or more lower alkyl groups;
- m is 1, 2, 3 or 4 and n is 0, 1, 2 or 3 with the proviso that the sum of m and n is 2, 3 or 4; and
- the pharmaceutically acceptable acid addition salts thereof.

As used in the specification and the appended claims, unless specified to the contrary, the following terms have the meaning indicated. The terms "lower alkyl" refers to a straight or branched chain monovalent substituent consisting solely of carbon and hydrogen, containing no unsaturation, and having from one to four carbon atoms. Examples of lower alkyl groups are methyl, ethyl, n-propyl, i-propyl, n-butyl, and t-butyl. The term "lower alkoxy" refers to a monovalent substituent containing oxygen and of the formula "lower alkyl—O—" wherein "lower alkyl" is as defined above.

Examples of lower alkoxy groups are methoxy, ethoxy, n-propoxy, i-propoxy, n-butoxy, and t-butoxy. The term "halo" refers to fluoro, chloro and bromo. The term "pharmaceutically acceptable acid addition salts" refers to salts of the subject compounds which possess the desired pharmacological or antimicrobial activity and which are neither biologically nor otherwise undesirable. These salts are formed with inorganic acids such as hydrochloric acid, hydrobromic acid, sulfuric acid, nitric acid or phosphoric acid, or organic acids such as acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like. The term "propylene" refers to 1,3-propylene.

It is also understood, for the purposes of this invention, that $R^1$ and Z cannot be substituted with three or more adjacent branched alkyl, branched alkoxy, and/or trifluoromethyl groups.

The compounds of formula (I) may be considered to consist of two subclasses, those of formulas (Ia) and (Ib) shown below:

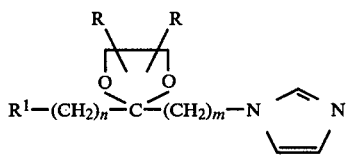

wherein $R^1$, m and n are as defined above and each R is independently hydrogen or lower alkyl, preferably wherein each R is hydrogen or each R is methyl or one R is lower alkyl and the other R is hydrogen, and

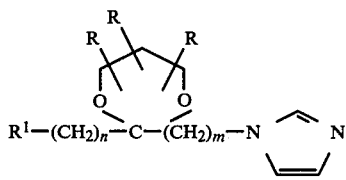

wherein $R^1$, m and n are as defined above and each R is independently hydrogen or lower alkyl.

Within the subclass represented by formula (Ib), preferred subgroups are those wherein each R is hydrogen or one R is lower alkyl and the other R's are hydrogen or one R is hydrogen and the other two R's are straight chain alkyl, preferably both on carbon 5. When each R is alkyl, methyl is preferred. Most particularly preferred are those compounds wherein each R is hydrogen or one R is methyl on carbon 4 or carbon 5 and the other R's are hydrogen or two R's are methyl and the other R is hydrogen, the methyl groups being on carbon 5.

One preferred subgenus of compounds of formulas (Ia) and (Ib) is that wherein n is two or three, the most preferred being wherein n is two. Within this subgenus one group of preferred compounds is that wherein m is one and n is two. Most preferred is 1-[[2-(2-(4-chlorophenyl)ethyl)-1,3-dioxolan-2yl]methyl]imidazole. Also within the above subgenus one group of preferred compounds includes that wherein $R^1$ is phenyl or phenyl substituted with halo, especially chloro, alkoxy, especially methoxy, or lower alkyl. For halo substituents, substitution at the 4-position is preferred and, when there is more than one halo substituent, it is preferred that all halo groups be the same, most preferably chloro. Preferred chloro substitution patterns for $R^1$ are 2-chloro, 4-chloro, 2,4-dichloro and 2,4,6-trichloro, with 4-chloro being most particularly preferred. For alkoxy substitution, 4-methoxy is preferred. For alkyl substituents on $R^1$, substitution at the four position is preferred and, when there is more than one alkyl substituent it is preferred that all alkyl groups be the same, most preferably methyl, particularly when $R^1$ is substituted with three, four or five alkyl groups. Preferred alkyl substitution patterns for $R^1$ are 2-methyl, 4-methyl, 2,4-dimethyl, 2,4,6-trimethyl, 2,5-dimethyl, with 4-methyl being most particularly preferred.

Certain compounds of formula (I) wherein Z is substituted by at least one lower alkyl may have geometric (cis and trans) isomers. The geometric isomers may be separated by various methods, for example, selective crystallization, column chromatography and high pressure liquid chromatography. Alternatively, where appropriate, the intermediates of formula (IV) (infra) may be separated and converted to the final cis or trans isomers of compounds of formula (I). Both geometric isomers as well as mixtures thereof are intended to be included within the scope of the present invention.

Certain compounds of formula (I) may also exist as optical isomers when the dioxolane ring or the dioxane ring does not possess a plane of symmetry, for example, compounds of formula (Ia) wherein one R is an alkyl group and the other R is hydrogen.

Accordingly, certain compounds of the present invention may be prepared in either optically active form, or as a racemic mixture. Unless otherwise specified, such compounds described herein are all in the racemic form. However, the scope of the subject invention herein is not to be considered limited to the racemic form but to encompass the individual optical isomers of the subject compounds.

If desired, racemic products prepared herein may be resolved into their optical antipodes by conventional resolution means known per se, for example, by the separation (e.g., fractional crystallization) of the diastereomeric salts formed by reaction of, e.g. racemic compounds of formula (I) with an optically active acid. Exemplary of such optically active acids are the optically active forms of camphor-10-sulfonic acid, α-bromocamphor-π-sulfonic acid, camphoric acid, menthoxyacetic acid, tartaric acid, malic acid, diacetyltartaric acid, pyrrolidone-5-carboxylic acid, dibenzoyltartaric acid, and the like. The separated pure diastereomeric salts may then be cleaved by standard means to afford the respective optical isomers of the compounds of formula (I).

Administration and Formulation

Another aspect of the present invention relates to pharmaceutical compositions useful for the treatment and/or prevention of convulsions in a mammalian subject comprising a compound of formula (I) or (II), or a pharmaceutically acceptable acid addition salt thereof, in admixture with a pharmaceutically acceptable non-toxic carrier.

Useful pharmaceutical carriers for the preparation of the pharmaceutical compositions hereof can be solids or liquids. Thus, the compositions can take the form of tablets, pills, capsules, powders, sustained release formulations, solutions, suspensions, elixirs, and the like.

Carriers can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Suitable pharmaceutical carriers and their formulations are described in "Remington's Pharmaceutical Sciences" by E. W. Martin. Such compositions will, in any event, contain a therapeutically effective amount of the active compound together with a suitable amount of carrier so as to prepare the proper dosage form for proper administration to the subject.

The therapeutically effective amount of the active compound can vary from 1 percent weight (%w) to 99%w or more of the active compound based on the total formulation and about 1%w to 99%w excipient. Preferably the active compound is present at a level of 20%-80%w.

Another aspect of the present invention relates to a method for treating and/or preventing convulsions in a mammalian subject comprising administering a therapeutically effective amount of a compound of formula (I) or formula (II), or a pharmaceutically acceptable acid addition salt thereof.

Compounds of formula (I) and (II) exhibit CNS related activity, in particular anticonvulsant activity. Initial anticonvulsant activity is determined using the maximal electroshock seizure test (J. Pharmacol. Exp. Ther. 96:99-113, 1949) or modifications thereof.

In the practice of the above described methods of the present invention a therapeutically effective amount of the compound of formula (I) or (II) or a pharmaceutical composition containing same is administered via any of the usual and acceptable methods known in the art, either singly or in combination with another compound or compounds of the present invention or other pharmaceutical agents. These compounds or compositions can thus be administered orally, systemically (i.e. intranasally or by suppository) or parenterally (i.e. intramuscularly, subcutaneously and intravenously), and can be administered either in the form of solid or liquid dosages including tablets, solutions, suspensions, and the like, as discussed in more detail hereinabove. Oral administration is preferred.

The formulation can be administered in a single unit dosage form for continuous treatment or prevention or in a single unit dosage form ad libitum when relief of symptoms is specifically required.

In view of the foregoing as well as in consideration of the degree of severity of the condition being treated, age of subject and so forth, all of which factors are determinable by routine experimentation by one skilled in the art, the effective dosage in accordance herewith can vary over a wide range. Generally, a therapeutically effective amount for anticonvulsant use ranges from about 0.1 to about 300 mg./kg. body weight per day and preferably from about 0.3 to about 100 mg./kg. body weight per day. In alternative terms, for an average adult human subject of about 70 kg. a therapeutically effective amount in accordance herewith would be, in preferred embodiments, from about 20 mg. to about 7 g. per day per subject.

Process of the Invention

Compounds of formula (I) are prepared by the reaction sequences shown below.

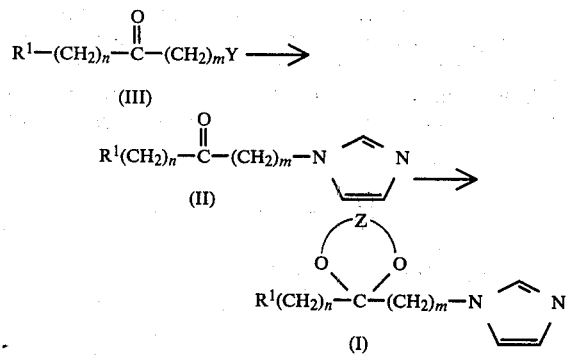

wherein $R^1$, Z, m and n are as previously defined and Y is a leaving group, such as halo (chloro or bromo) or a sulfonate ester.

This reaction sequence is particularly useful for preparing compounds wherein n is 1 or greater.

(a) The halo ketones of formula (III) are generally known or are readily prepared using the methods disclosed in U.S. Pat. No. 4,078,071. The halo ketones wherein m is one and n is one or two are also conveniently prepared by oxidizing the corresponding halo alcohols, e.g. with Jones reagent. The halo alcohols are prepared by the method described in J. Med. Chem. 1978, 21, 840, and J. Amer. Chem. Soc. 1930, 52, 1164.

(b) The imidazole ketones of formula (II) are prepared according to the methods disclosed in U.S. Pat. No. 4,078,071, in particular by the methods disclosed in reaction schemes B, C, D, E, F and H. An additional useful method of making the vinyl ketone precursors for the reaction scheme C in U.S. Pat. No. 4,078,071 consists of oxidation of a terminal olefin using selenium dioxide, with or without added t-butyl hydroperoxide (J. Amer. Chem. Soc. 1977, 99, 5526) followed by oxidation of the resulting vinyl alcohol.

Compounds of formula (II) may also be prepared by oxidizing the alcohols of formula (V)

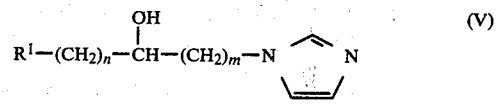

wherein $R^1$ is as defined above by the method described in J. Org. Chem. 1979, 44(23), 4148. Dimethyl sulfoxide is reacted with oxalyl chloride at $-100°$ to $-60°$ C. The intermediate formed is reacted with the alcohol of formula (V) to form an alkoxy sulfonium salt which is converted to the ketone of formula (II) upon addition of triethylamine.

(c) Compounds of formula (II) are ketalized by treatment of the ketone (or an acid addition salt thereof) with the desired dihydric alcohol in the presence of 1.02 molar equivalents to 2 molar equivalents of an acid or a Lewis acid, e.g. p-toluenesulfonic acid, perchloric acid, fuming sulfuric acid, boron trifluoride, zinc chloride and the like. When the acid addition salt of compounds of formula (II) is used, correspondingly less acid or Lewis acid (i.e. 0.02 to 1 molar equivalents) is required. In either case, p-toluenesulfonic acid is particularly preferred. The reaction is generally carried out using from 1 to 10 moles, preferably from 1 to 5 moles of dihydric alcohol relative to one mole of the ketone. Water is preferably removed as an azeotrope with a solvent, for example a hydrocarbon such as cyclohexane or an aromatic hydrocarbon such as benzene or toluene, at a temperature sufficient to effect such azeotropic removal, e.g. from about 75° to about 150° C.

Compounds of formula (I) may also be prepared by the procedure depicted in the following reaction sequence.

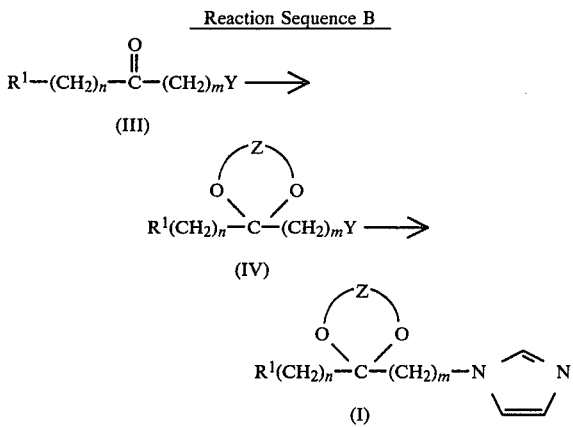

Reaction Sequence B wherein $R^1$, Z, m and n and Y are as previously defined. This method is particularly preferred when n is O, but it may also be used for all values of m and n.

(d) The halo ketones of formula (III) are ketalized to compounds of formula (IV) under similar reaction conditions as is described in (C) above except that only a catalytic amount of acid, e.g. about 0.01 to about 0.2 molar equivalents is used.

(e) The imidazole ketals of formula (I) are prepared by reacting the compounds of formula (IV) with imidazole and/or an imidazole salt, preferably an alkali metal salt, e.g. the sodium salt of imidazole in an inert organic solvent such as dimethylformamide, dimethyl acetamide, hexamethylphosphoramide, tetrahydrofuran and the like at a temperature between 20° C. and 165° C. The reaction is generally carried out using from 1 to 5 moles of imidazole and/or 1 to 2 moles of the metal salt thereof relative to one mole of the compound of formula (IV).

Compounds of formula (III) are also ketalized to compounds of formula (IV) by the method described in Synthesis, 1974, 23. A ketone of formula (III) is reacted with the desired dihydric alcohol in a molar ratio of about 1:1 in an excess of a simple alcohol, for example methanol, ethanol, 1-butanol or benzyl alcohol in the presence of a catalytic amount of an acid or a Lewis acid, e.g. p-toluenesulfonic acid, boron trifluoride, tin (IV) chloride and the like to form the cyclic ketal.

The cyclic ketals may also be prepared by other methods known in the art, such as by exchange with the ketal of a low boiling ketone.

The dihydric alcohols used in the above reaction sequences are generally available e.g. from Aldrich Chemical Co. The 1,2-diols which are not readily available may be prepared according to known procedures as described in British Pat. No. 1,528,639. The 1,3-diols which are not readily available may be prepared according to the Prins Reaction as described in The Merck Index, 9th Ed., 1976, ONR-71, or methods well known in the art.

The subject compounds of the instant invention can be isolated as free bases; however since many of the compounds in base form are oils, it is often more convenient to isolate and further characterize the compounds as acid addition salts. These salts are prepared in the usual manner, i.e., by reaction of the compound with a suitable inorganic or organic acid, described above. If desired, the salts can be readily converted to the compounds in base form by treatment with a base, such as potassium or sodium carbonate or potassium or sodium hydroxide.

The ketone intermediates of formula (II) and the pharmaceutically acceptable acid addition salts thereof are also useful as anticonvulsant agents and may be administered in the manner and at the dosage levels as discussed hereinabove for compounds of formula (I).

PREPARATION 1

1-Chloro-4-(4-chlorophenyl)-2-butanone (110 g.) was added portionwise over half an hour to a stirred suspension of imidazole (175 g) in dimethylformamide (150 ml) at 0° C. and the mixture stirred overnight at ambient temperature. The resulting solution was poured into water (1500 ml) with seeding at the first sign of turbidity, and the precipitate filtered off and washed well with water and hexane. Chromatography of the product on silica gel (1 Kg.), eluting with 7% methanol in methylene chloride gave 100 g of 1-[4-(4-chlorophenyl)butan-2-on-1-yl]imidazole.

The hydrochloride salt from acetone/methanol had m.p. 172.5°–174° C.

Similarly, proceeding as above, substituting the appropriate haloketone for 1-chloro-4-(4-chlorophenyl)-2-butanone, the following compounds may be prepared:
1-[4-phenylbutan-2-on-1-yl]imidazole-hydrochloride salt, m.p. 171°–173° C.,
1-[4-(4-fluorophenyl)butan-2-on-1-yl]imidazole,
1-[4-(2-chlorophenyl)butan-2-on-1-yl]imidazole,
1-[4-(3-chlorophenyl)butan-2-on-1-yl]imidazole,
1-[4-(2,4-dichlorophenyl)butan-2-on-1-yl]imidazole,
1-[4-(2,4,6-trichlorophenyl)butan-2-on-1-yl]imidazole,
1-[4-(3-methylphenyl)butan-2-on-1-yl]imidazole,
1-[4-(4-methylphenyl)butan-2-on-1-yl]imidazole-hydrochloride salt, m.p. 160°–162.5° C.,
1-[4-(4-i-propylphenyl)butan-2-on-1-yl]imidazole,
1-[4-(4-t-butylphenyl)butan-2-on-1-yl]imidazole,
1-[4-(2,4-dimethylphenyl)butan-2-on-1-yl]imidazole,
1-[4-(3,5-dimethylphenyl)butan-2-on-1-yl]imidazole,
1-[4-(2,4,6-trimethylphenyl)butan-2-on-1-yl]imidazole,
1-[4-(2,3,5,6-tetramethylphenyl)butan-2-on-1-yl]imidazole,
1-[4-(2,3,4,5,6-pentamethylphenyl)butan-2-on-1-yl]imidazole,
1-[4-(3-methoxyphenyl)butan-2-on-1-yl]imidazole,
1-[4-(4-methoxyphenyl)butan-2-on-1-yl]imidazole-hydrobromide salt, m.p. 145.5°–147.5° C.,
1-[4-(4-n-butoxyphenyl)butan-2-on-1-yl]imidazole,
1-[4-phenylbutan-3-on-1-yl]imidazole,
1-[4-(4-chlorophenyl)butan-3-on-1-yl]imidazole,
1-[4-(4-bromophenyl)butan-3-on-1-yl]imidazole,
1-[4-(2,4-dichlorophenyl)butan-3-on-1-yl]imidazole,
1-[4-(3-methylphenyl)butan-3-on-1-yl]imidazole,
1-[4-(4-methylphenyl)butan-3-on-1-yl]imidazole,
1-[4-(4-t-butylphenyl)butan-3-on-1-yl]imidazole,
1-[4-(2,4-dimethylphenyl)butan-3-on-1-yl]imidazole,
1-[4-(3,5-dimethylphenyl)butan-3-on-1-yl]imidazole, 1-[4-(2,4,6-trimethylphenyl)butan-3-on-1-yl]imidazole,
1-[4-(2,3,5,6-tetramethylphenyl)butan-3-on-1-yl]imidazole,
1-[4-(2,3,4,5,6-pentamethylphenyl)butan-3-on-1-yl]imidazole,
1-[4-(3-methoxyphenyl)butan-3-on-1-yl]imidazole,
1-[4-(4-methoxyphenyl)butan-3-on-1-yl]imidazole,
1-[4-(4-n-butoxyphenyl)butan-3-on-1-yl]imidazole,
1-[3-phenylpropan-2-on-1-yl]imidazole,
1-[3-(4-chlorophenyl)propan-2-on-1-yl]imidazole,
1-[3-(3-methylphenyl)propan-2-on-1-yl]imidazole,
1-[3-(4-methylphenyl)propan-2-on-1-yl]imidazole,
1-[3-(4-i-propylphenyl)propan-2-on-1-yl]imidazole,
1-[3-(4-t-butylphenyl)propan-2-on-1-yl]imidazole,
1-[3-(2,4-dimethylphenyl)propan-2-on-1-yl]imidazole,
1-[3-(3,5-dimethylphenyl)propan-2-on-1-yl]imidazole,
1-[3-(2,4,6-trimethylphenyl)propan-2-on-1-yl]imidazole,
1-[3-(2,3,5,6-tetramethylphenyl)propan-2-on-1-yl]imidazole,
1-[3-(2,3,4,5,6-pentamethylphenyl)propan-2-on-1-yl]imidazole,
1-[3-(3-methoxyphenyl)propan-2-on-1-yl]imidazole,
1-[3-(4-methoxyphenyl)propan-2-on-1-yl]imidazole,
1-[3-(4-t-butoxyphenyl)propan-2-on-1-yl]imidazole,
1-[5-phenylpentan-2-on-1-yl]imidazole,
1-[5-(4-methylphenyl)pentan-2-on-1-yl]imidazole,
1-[5-(4-chlorophenyl)pentan-2-on-1-yl]imidazole,
1-[5-(4-methoxyphenyl)pentan-2-on-1-yl]imidazole,
1-[5-phenylpentan-3-on-1-yl]imidazole,
1-[5-(4-methylphenyl)pentan-3-on-1-yl]imidazole,
1-[5-(4-chlorophenyl)pentan-3-on-1-yl]imidazole,
1-[5-(4-methoxyphenyl)pentan-3-on-1-yl]imidazole,
1-[5-phenylpentan-4-on-1-yl]imidazole,
1-[5-(4-methylphenyl)pentan-4-on-1-yl]imidazole,
1-[5-(4-chlorophenyl)pentan-4-on-1-yl]imidazole,
1-[5-(4-methoxyphenyl)pentan-4-on-1-yl]imidazole,

PREPARATION 2

A mixture of 1-(4-chlorophenyl)-3-chloro-1-propanone (β,p-dichloropropiophenone) (2.03 g), ethylene glycol (5 ml) and p-toluenesulfonic acid (10 mg) in benzene (20 ml) were heated under reflux through a Dean-Stark trap for 4 hours. The trap was dried, filled with 3 A molecular sieves and heating continued overnight. After removal of the solvent, excess aqueous potassium carbonate was added. The product was extracted with ether and the extracts washed well with water and dried (MgSO$_4$). Evaporation of the solvent gave 2-(2-chloroethyl)-2-(4-chlorophenyl)-1,3-dioxolane.

Similarly, proceeding as above substituting the appropriate halo ketone for 1-(4-chlorophenyl)-3-chloro-1-propanone, and substituting the appropriate diol for ethylene glycol, the following compounds may be prepared:

2-(3-bromopropyl)-2-phenyl-1,3-dioxolane,
2-(3-bromopropyl)-2-(4-chlorophenyl)-1,3-dioxolane,
2-(3-bromopropyl)-2-(4-methylphenyl)-1,3-dioxolane,
2-(3-bromopropyl)-2-(4-i-propylphenyl)-1,3-dioxolane,
2-(3-bromopropyl)-2-(4-methoxyphenyl)-1,3-dioxolane,
2-(3-bromopropyl)-2-(4-n-propoxyphenyl)-1,3-dioxolane,
2-(3-bromopropyl)-2-phenyl-4-methyl-1,3-dioxolane,
2-(3-bromopropyl)-2-(4-chlorophenyl)-4-methyl-1,3-dioxolane,
2-(3-bromopropyl)-2-(4-methylphenyl)-4-methyl-1,3-dioxolane,
2-(3-bromopropyl)-2-(4-i-propylphenyl)-4-methyl-1,3-dioxolane,
2-(3-bromopropyl)-2-(4-methoxyphenyl)-4-methyl-1,3-dioxolane,
2-(3-bromopropyl)-2-(4-n-propoxyphenyl)-4-methyl-1,3-dioxolane,
2-(3-bromopropyl)-2-phenyl-4,5-dimethyl-1,3-dioxolane,
2-(3-bromopropyl)-2-(4-chlorophenyl)-4,5-dimethyl-1,3-dioxolane,
2-(3-bromopropyl)-2-(4-methylphenyl)-4,5-dimethyl-1,3-dioxolane,
2-(3-bromopropyl)-2-(4-i-propylphenyl)-4,5-dimethyl-1,3-dioxolane,
2-(3-bromopropyl)-2-(4-methoxyphenyl)-4,5-dimethyl-1,3-dioxolane,
2-(3-bromopropyl)-2-(4-n-propoxyphenyl)-4,5-dimethyl-1,3-dioxolane,
2-(3-bromopropyl)-2-phenyl-1,3-dioxane,
2-(3-bromopropyl)-2-(4-chlorophenyl)-1,3-dioxane,
2-(3-bromopropyl)-2-(4-methylphenyl)-1,3-dioxane,
2-(3-bromopropyl)-2-(4-i-propylphenyl)-1,3-dioxane,
2-(3-bromopropyl)-2-(4-methoxyphenyl)-1,3-dioxane,
2-(3-bromopropyl)-2-(4-n-propoxyphenyl)-1,3-dioxane,
2-(3-bromopropyl)-2-phenyl-5,5-dimethyl-1,3-dioxane,
2-(3-bromopropyl)-2-(4-chlorophenyl)-5,5-dimethyl-1,3-dioxane,
2-(3-bromopropyl)-2-(4-methylphenyl)-5,5-dimethyl-1,3-dioxane,
2-(3-bromopropyl)-2-(4-i-propylphenyl)-5,5-dimethyl-1,3-dioxane,
2-(3-bromopropyl)-2-(4-methoxyphenyl)-5,5-dimethyl-1,3-dioxane,
2-(3-bromopropyl)-2-(4-n-propoxyphenyl)-5,5-dimethyl-1,3-dioxane,
2-(2-chloroethyl)-2-phenyl-1,3-dioxolane,
2-(2-chloroethyl)-2-(3-chlorophenyl)-1,3-dioxolane,
2-(2-chloroethyl)-2-(4-fluorophenyl)-1,3-dioxolane,
2-(2-chloroethyl)-2-(4-methylphenyl)-1,3-dioxolane,
2-(2-chloroethyl)-2-(4-t-butylphenyl)-1,3-dioxolane,
2-(2-chloroethyl)-2-(4-methoxyphenyl)-1,3-dioxolane,
2-(2-chloroethyl)-2-(4-n-propoxyphenyl)-1,3-dioxolane,
2-(2-chloroethyl)-2-phenyl-4-methyl-1,3-dioxolane,
2-(2-chloroethyl)-2-(4-chlorophenyl)-4-methyl-1,3-dioxolane,
2-(2-chloroethyl)-2-(4-methylphenyl)-4-methyl-1,3-dioxolane,
2-(2-chloroethyl)-2-(4-t-butylphenyl)-4-methyl-1,3-dioxolane,
2-(2-chloroethyl)-2-(4-methoxyphenyl)-4-methyl-1,3-dioxolane,
2-(2-chloroethyl)-2-(4-n-propoxyphenyl)-4-methyl-1,3-dioxolane,
2-(2-chloroethyl)-2-phenyl-4,5-dimethyl-1,3-dioxolane,
2-(2-chloroethyl)-2-(4-chlorophenyl)-4,5-dimethyl-1,3-dioxolane,
2-(2-chloroethyl)-2-(4-methylphenyl)-4,5-dimethyl-1,3-dioxolane,
2-(2-chloroethyl)-2-(4-t-butylphenyl)-4,5-dimethyl-1,3-dioxolane,
2-(2-chloroethyl)-2-(4-methoxyphenyl)-4,5-dimethyl-1,3-dioxolane,
2-(2-chloroethyl)-2-(4-n-propoxyphenyl)-4,5-dimethyl-1,3-dioxolane,
2-(2-chloroethyl)-2-phenyl-1,3-dioxane,
2-(2-chloroethyl)-2-(4-chlorophenyl)-1,3-dioxane,
2-(2-chloroethyl)-2-(4-methylphenyl)-1,3-dioxane,
2-(2-chloroethyl)-2-(4-t-butylphenyl)-1,3-dioxane, 2-(2-chloroethyl)-2-(4-methoxyphenyl)-1,3-dioxane,
2-(2-chloroethyl)-2-(4-n-propoxyphenyl)-1,3-dioxane,
2-(2-chloroethyl)-2-phenyl-5,5-dimethyl-1,3-dioxane,
2-(2-chloroethyl)-2-(4-chlorophenyl)-5,5-dimethyl-1,3-dioxane,
2-(2-chloroethyl)-2-(4-methylphenyl)-5,5-dimethyl-1,3-dioxane,
2-(2-chloroethyl)-2-(4-t-butylphenyl)-5,5-dimethyl-1,3-dioxane,
2-(2-chloroethyl)-2-(4-methoxyphenyl)-5,5-dimethyl-1,3-dioxane,
2-(2-chloroethyl)-2-(4-n-propoxyphenyl)-5,5-dimethyl-1,3-dioxane,
2-(4-chlorobutyl)-2-phenyl-1,3-dioxolane,
2-(4-chlorobutyl)-2-(4-chlorophenyl)-1,3-dioxolane,
2-(4-chlorobutyl)-2-(4-methylphenyl)-1,3-dioxolane,
2-(4-chlorobutyl)-2-(4-methoxyphenyl)-1,3-dioxolane,
2-(4-chlorobutyl)-2-phenyl-4-methyl-1,3-dioxolane,
2-(4-chlorobutyl)-2-(4-chlorophenyl)-4-methyl-1,3-dioxolane,
2-(4-chlorobutyl)-2-(4-methylphenyl)-4-methyl-1,3-dioxolane,
2-(4-chlorobutyl)-2-(4-methoxyphenyl)-4-methyl-1,3-dioxolane,
2-(4-chlorobutyl)-2-phenyl-4,5-dimethyl-1,3-dioxolane,
2-(4-chlorobutyl)-2-(4-chlorophenyl)-4,5-dimethyl-1,3-dioxolane,
2-(4-chlorobutyl)-2-(4-methylphenyl)-4,5-dimethyl-1,3-dioxolane,
2-(4-chlorobutyl)-2-(4-methoxyphenyl)-4,5-dimethyl-1,3-dioxolane,
2-(4-chlorobutyl)-2-phenyl-1,3-dioxane,
2-(4-chlorobutyl)-2-(4-chlorophenyl)-1,3-dioxane,
2-(4-chlorobutyl)-2-(4-methylphenyl)-1,3-dioxane,
2-(4-chlorobutyl)-2-(4-methoxyphenyl)-1,3-dioxane,
2-(4-chlorobutyl)-2-phenyl-5,5-dimethyl-1,3-dioxane,
2-(4-chlorobutyl)-2-(4-chlorophenyl)-5,5-dimethyl-1,3-dioxane,
2-(4-chlorobutyl)-2-(4-methylphenyl)-5,5-dimethyl-1,3-dioxane,
2-(4-chlorobutyl)-2-(4-methoxyphenyl)-5,5-dimethyl-1,3-dioxane.

The following specific examples are illustrative of the present invention and should not be considered as limitative thereof in any manner.

EXAMPLE 1

(a) A mixture of 1-[4-(4-chlorophenyl)butan-2-on-1-yl]imidazole (2.0 g), ethylene glycol (1.0 g) and anhydrous p-toluenesulfonic acid (2.77 g) in toluene (30 ml) was heated under reflux through a Dean-Stark trap for 2 hours. The resulting mixture was poured into aqueous potassium carbonate solution, extracted with ether (2×100 ml) and the extracts dried (MgSO₄). The hydrochloride salt was formed by dropwise addition of ethereal hydrogen chloride until precipitation was complete, and was recrystallized from acetone/methanol to give 1-[[2-(2-(4-chlorophenyl)ethyl)-1,3-dioxolan-2-yl]methyl]imidazole hydrochloride, m.p. 174.5°–175.5° C.

(b) Similarly, proceeding as in part (a) above substituting the appropriate ketone for 1-[4-(4-chlorophenyl)-butan-2-on-1-yl]imidazole there are obtained the following compounds. Where indicated, the compounds are further characterized by conversion to the indicated acid addition salt.

1-[[2-(2-phenylethyl)-1,3-dioxolan-2-yl]methyl]-imidazole, -hydrobromide salt, m.p. 165°–167° C.,
1-[[2-(2-(4-fluorophenyl)ethyl)-1,3-dioxolan-2-yl]methyl]imidazole,
1-[[2-(2-(2-chlorophenyl)ethyl)-1,3-dioxolan-2-yl]methyl]imidazole,
1-[[2-(2-(3-chlorophenyl)ethyl)-1,3-dioxolan-2-yl]methyl]imidazole,
1-[[2-(2-(2,4-dichlorophenyl)ethyl)-1,3-dioxolan-2-yl]methyl]imidazole,
1-[[2-(2-(2,4,6-trichlorophenyl)ethyl)-1,3-dioxolan-2-yl]methyl]imidazole,
1-[[2-(2-(3-methylphenyl)ethyl)-1,3-dioxolan-2-yl]methyl]imidazole,
1-[[2-(2-(4-methylphenyl)ethyl)-1,3-dioxolan-2-yl]methyl]imidazole-nitrate salt, m.p. 128°–130.5° C.,
1-[[2-(2-(4-i-propylphenyl)ethyl)-1,3-dioxolan-2-yl]methyl]imidazole,
1-[[2-(2-(4-t-butylphenyl)ethyl)-1,3-dioxolan-2-yl]methyl]imidazole,
1-[[2-(2-(2,4-dimethylphenyl)ethyl)-1,3-dioxolan-2-yl]methyl]imidzole,
1-[[2-(2-(3,5-dimethylphenyl)ethyl)-1,3-dioxolan-2-yl]methyl]imidazole,
1-[[2-(2-(2,4,6-trimethylphenyl)ethyl)-1,3-dioxolan-2-yl]methyl]imidazole,
1-[[2-(2-(2,3,5,6-tetramethylphenyl)ethyl)-1,3-dioxolan-2-yl]methyl]imidazole,
1-[[2-(2-(2,3,4,5,6-pentamethylphenyl)ethyl)-1,3-dioxolan-2-yl]methyl]imidazole,
1-[[2-(2-(3-methoxyphenyl)ethyl)-1,3-dioxolan-2-yl]methyl]imidazole,
1-[[2-(2-(4-methoxyphenyl)ethyl)-1,3-dioxolan-2-yl]methyl]imidazole-hydrochloride salt, m.p. 168.5°–170° C.,
1-[[2-(2-(4-n-butoxyphenyl)ethyl)-1,3-dioxolan-2-yl]methyl]imidazole,
1-[2-(2-benzyl-1,3-dioxolan-2-yl)ethyl]imidazole-hydrochloride salt, m.p. 151°–153° C.,
1-[2-(2-(4-chlorobenzyl)-1,3-dioxolan-2-yl)ethyl]imidazole,
1-[2-(2-(4-bromobenzyl)-1,3-dioxolan-2-yl)ethyl]imidazole,
1-[2-(2-(2,4-dichlorobenzyl)-1,3-dioxolan-2-yl)ethyl]imidazole,
1-[2-(2-(3-methylbenzyl)-1,3-dioxolan-2-yl)ethyl]imidazole,
1-[2-(2-(4-methylbenzyl)-1,3-dioxolan-2-yl)ethyl]imidazole,
1-[2-(2-(4-t-butylbenzyl)-1,3-dioxolan-2-yl)ethyl]imidazole,
1-[2-(2-(2,4-dimethylbenzyl)-1,3-dioxolan-2-yl)ethyl]imidazole,
1-[2-(2-(3,5-dimethylbenzyl)-1,3-dioxolan-2-yl)ethyl]imidazole,
1-[2-(2-(2,4,6-trimethylbenzyl)-1,3-dioxolan-2-yl)ethyl]imidazole,
1-[2-(2-(2,3,5,6-tetramethylbenzyl)-1,3-dioxolan-2-yl)ethyl]imidazole,
1-[2-(2-(2,3,4,5,6-pentamethylbenzyl)-1,3-dioxolan-2-yl)ethyl]imidazole,
1-[2-(2-(3-methoxybenzyl)-1,3-dioxolan-2-yl)ethyl]imidazole,
1-[2-(2-(4-methoxybenzyl)-1,3-dioxolan-2-yl)ethyl]imidazole,
1-[2-(2-(4-n-butoxybenzyl)-1,3-dioxolan-2-yl)ethyl]imidazole,
1-[[2-benzyl-1,3-dioxolan-2-yl]methyl]imidazole-hydrobromide salt, m.p. 191.5°–195.5° C., 1-[[2-(4-chlorobenzyl)-1,3-dioxolan-2-yl]methyl-]imidazole-hydrobromide salt, m.p. 184°–186° C.,
1-[[2-(3-methylbenzyl)-1,3-dioxolan-2-yl]methyl-]imidazole,
1-[[2-(4-methylbenzyl)-1,3-dioxolan-2-yl]methyl-]imidazole-hydrobromide salt, m.p. 205°–206° C.,
1-[[2-(4-i-propylbenzyl)-1,3-dioxolan-2-yl]methyl-]imidazole,
1-[[2-(4-t-butylbenzyl)-1,3-dioxolan-2-yl]methyl-]imidazole,
1-[[2-(2,4-dimethylbenzyl)-1,3-dioxolan-2-yl]methyl-]imidazole,
1-[[2-(3,5-dimethylbenzyl)-1,3-dioxolan-2-yl]methyl-]imidazole,
1-[[2-(2,4,6-trimethylbenzyl)-1,3-dioxolan-2-yl]methyl-]imidazole,
1-[[2-(2,3,5,6-tetramethylbenzyl)-1,3-dioxolan-2-yl]methyl]imidazole,
1-[[2-(2,3,4,5,6-pentamethylbenzyl)-1,3-dioxolan-2-yl]methyl]imidazole,
1-[[2-(3-methoxybenzyl)-1,3-dioxolan-2-yl]methyl-]imidazole,
1-[[2-(4-methoxybenzyl)-1,3-dioxolan-2-yl]methyl-]imidazole,
1-[[2-(4-t-butoxybenzyl)-1,3-dioxolan-2-yl]methyl-]imidazole,
1-[[2-(3-phenylpropyl)-1,3-dioxolan-2-yl]methyl-]imidazole,
1-[[2-(3-(4-methylphenyl)propyl)-1,3-dioxolan-2-yl]methyl]imidazole,
1-[[2-(3-(4-chlorophenyl)propy)-1,3-dioxolan-2-yl]methyl]imidazole,
1-[[2-(3-(4-methoxyphenyl)propyl)-1,3-dioxolan-2-yl]methyl]imidazole,
1-[2-(2-(2-phenylethyl)-1,3-dioxolan-2-yl)ethyl-]imidazole,
1-[2-(2-(2-(4-methylphenyl)ethyl)-1,3-dioxolan-2-yl)ethyl]imidazole,
1-[2-(2-(2-(4-chlorophenyl)ethyl)-1,3-dioxolan-2-yl)ethyl]imidazole,
1-[2-(2-(2-(4-methoxyphenyl)ethyl)-1,3-dioxolan-2-yl)ethyl]imidazole,
1-[3-(2-benzyl-1,3-dioxolan-2-yl)-n-propyl]imidazole,
1-[3-(2-(4-methylbenzyl)-1,3-dioxolan-2-yl)-n-propyl-]imidazole,
1-[3-(2-(4-chlorobenzyl)-1,3-dioxolan-2-yl)-n-propyl-]imidazole,
1-[3-(2-(4-methoxybenzyl)-1,3-dioxolan-2-yl)-n-propyl-]imidazole.

(c) Substituting 1,2-propanediol for ethylene glycol in part (a) of this example there is prepared 1-[[2-(2-(4-chlorophenyl)ethyl)-4-methyl-1,3-dioxolan-2-yl]methyl]imidazole-hydrobromide salt, m.p. 199°–200° C. By substituting the appropriate ketone for 1-[4-(4-chlorophenyl)butan-2-on-1-yl]imidazole and substituting 1,2-propanediol for ethylene glycol in part
(a) of this example the following compounds are prepared:

1-[[2-(2-phenylethyl)-4-methyl-1,3-dioxolan-2-yl]methyl]imidazole-hydrobromide salt, m.p. 189°–193° C.,
1-[[2-(2-(4-fluorophenyl)ethyl)-4-methyl-1,3-dioxolan-2-yl]methyl]imidazole,
1-[[2-(2-(2-chlorophenyl)ethyl)-4-methyl-1,3-dioxolan-2-yl]methyl]imidazole,
1-[[2-(2-(3-chlorophenyl)ethyl)-4-methyl-1,3-dioxolan-2-yl]methyl]imidazole,
1-[[2-(2-(2,4-dichlorophenyl)ethyl)-4-methyl-1,3-dioxolan-2-yl]methyl]imidazole,
1-[[2-(2-(2,4,6-trichlorophenyl)ethyl)-4-methyl-1,3-dioxolan-2-yl]methyl]imidazole,
1-[[2-(2-(3-methylphenyl)ethyl)-4-methyl-1,3-dioxolan-2-yl]methyl]imidazole,
1-[[2-(2-(4-methylphenyl)ethyl)-4-methyl-1,3-dioxolan-2-yl]methyl]imidazole,
1-[[2-(2-(4-i-propylphenyl)ethyl)-4-methyl-1,3-dioxolan-2-yl]methyl]imidazole,
1-[[2-(2-(4-t-butylphenyl)ethyl)-4-methyl-1,3-dioxolan-2-yl]methyl]imidazole,
1-[[2-(2-(2,4-dimethylphenyl)ethyl)-4-methyl-1,3-dioxolan-2-yl]methyl]imidazole,
1-[[2-(2-(3,5-dimethylphenyl)ethyl)-4-methyl-1,3-dioxolan-2-yl]methyl]imidazole,
1-[[2-(2-(2,4,6-trimethylphenyl)ethyl)-4-methyl-1,3-dioxolan-2-yl]methyl]imidazole,
1-[[2-(2-(2,3,5,6-tetramethylphenyl)ethyl)-4-methyl-1,3-dioxolan-2-yl]methyl]imidazole,
1-[[2-(2-(2,3,4,5,6-pentamethylphenyl)ethyl-4-methyl-1,3-dioxolan-2-yl]methyl]imidazole,
1-[[2-(2-(3-methoxyphenyl)ethyl)-4-methyl-1,3-dioxolan-2-yl]methyl]imidazole,
1-[[2-(2-(4-methoxyphenyl)ethyl)-4-methyl-1,3-dioxolan-2-yl]methyl]imidazole,
1-[[2-(2-(4-n-butoxyphenyl)ethyl)-4-methyl-1,3-dioxolan-2-yl]methyl]imidazole,
1-[[2-(2-benzyl-4-methyl-1,3-dioxolan-2-yl]ethyl-]imidazole,
1-[2-(2-(4-chlorobenzyl)-4-methyl-1,3-dioxolan-2-yl)ethyl]imidazole,
1-[2-(2-(4-bromobenzyl)-4-methyl-1,3-dioxolan-2-yl)ethyl]imidazole,
1-[2-(2-(2,4-dichlorobenzyl)-4-methyl-1,3-dioxolan-2-yl)ethyl]imidazole,
1-[2-(2-(3-methylbenzyl)-4-methyl-1,3-dioxolan-2-yl)ethyl]imidazole,
1-[2-(2-(4-methylbenzyl)-4-methyl-1,3-dioxolan-2-yl)ethyl]imidazole,
1-[2-(2-(4-t-butylbenzyl)-4-methyl-1,3-dioxolan-2-yl)ethyl]imidazole,
1-[2-(2-(2,4-dimethylbenzyl)-4-methyl-1,3-dioxolan-2-yl)ethyl]imidazole,
1-[2-(2-(3,5-dimethylbenzyl)-4-methyl-1,3-dioxolan-2-yl)ethyl]imidazole,
1-[2-(2-(2,4,6-trimethylbenzyl)-4-methyl-1,3-dioxolan-2-yl)ethyl]imidazole,
1-[2-(2-(2,3,5,6-tetramethylbenzyl)-4-methyl-1,3-dioxolan-2-yl)ethyl]imidazole,
1-[2-(2-(2,3,4,5,6-pentamethylbenzyl)-4-methyl-1,3-dioxolan-2-yl)ethyl]imidazole,
1-[2-(2-(3-methoxybenzyl)-4-methyl-1,3-dioxolan-2-yl)ethyl]imidazole,
1-[2-(2-(4-methoxybenzyl)-4-methyl-1,3-dioxolan-2-yl)ethyl]imidazole,
1-[2-(2-(4-n-butoxybenzyl)-4-methyl-1,3-dioxolan-2-yl)ethyl]imidazole,
1-[[2-benzyl-4-methyl-1,3-dioxolan-2-yl]methyl-]imidazole,
1-[[2-(4-chlorobenzyl)-4-methyl-1,3-dioxolan-2-yl]methyl]imidazole,
1-[[2-(3-methylbenzyl)-4-methyl-1,3-dioxolan-2yl]methyl]imidazole,
1-[[2-(4-methylbenzyl)-4-methyl-1,3-dioxolan-2-yl]methyl]imidazole-hydrobromide salt, m.p. 199°–205° C.,
1-[[2-(4-i-propylbenzyl)-4-methyl-1,3-dioxolan-2-yl]methyl]imidazole,
1-[[2-(4-t-butylbenzyl)-4-methyl-1,3-dioxolan-2-yl]methyl]imidazole, 1-[[2-(2,4-dimethylbenzyl)-4-methyl-1,3-dioxolan-2-yl]methyl]imidazole,
1-[[2-(2,4,6-trimethylbenzyl)-4-methyl-1,3-dioxolan-2-yl]methyl]imidazole,
1-[[2-(2,3,5,6-tetramethylbenzyl)-4-methyl-1,3-dioxolan-2-yl]methyl]imidazole,
1-[[2-(2,3,4,5,6-pentamethylbenzyl)-4-methyl-1,3-dioxolan-2-yl]methyl]imidazole,
1-[[2-(3-methoxybenzyl)-4-methyl-1,3-dioxolan-2-yl]methyl]imidazole,
1-[[2-(4-methoxybenzyl)-4-methyl-1,3-dioxolan-2-yl]methyl]imidazole,
1-[[2-(4-t-butoxybenzyl)-4-methyl-1,3-dioxolan-2-yl]methyl]imidazole,
1-[[2-(3-phenylpropyl)-4-methyl-1,3-dioxolan-2-yl]methyl]imidazole,
1-[[2-(3-(4-methylphenyl)propyl)-4-methyl-1,3-dioxolan-2-yl]methyl]imidazole,
1-[[2-(3-(4-chlorophenyl)propyl)-4-methyl-1,3-dioxolan-2-yl]methyl]imidazole,
1-[[2-(3-(4-methoxyphenyl)propyl)-4-methyl-1,3-dioxolan-2-yl]methyl]imidazole,
1-[2-(2-(2-phenylethyl)-4-methyl-1,3-dioxolan-2-yl)ethyl]imidazole,
1-[2-(2-(2-(4-methylphenyl)ethyl)-4-methyl-1,3-dioxolan-2-yl)ethyl]imidazole,
1-[2-(2-(2-(4-chlorophenyl)ethyl)-4-methyl-1,3-dioxolan-2-yl)ethyl]imidazole,
1-[2-(2-(2-(4-methoxyphenyl)ethyl)-4-methyl-1,3-dioxolan-2-yl)ethyl]imidazole,
1-[3-(2-benzyl-4-methyl-1,3-dioxolan-2-yl)-n-propyl]imidazole,
1-[3-(2-(4-methylbenzyl)-4-methyl-1,3-dioxolan-2-yl)-n-propyl]imidazole,
1-[3-(2-(4-chlorobenzyl)-4-methyl-1,3-dioxolan-2-yl)-n-propyl]imidazole,
1[3-(2-(4-methoxybenzyl)-4-methyl-1,3-dioxolan-2-yl)-n-propyl]imidazole.

(d) Substituting 1,2-butanediol for ethylene glycol in part (a) of this example there is prepared 1-[[2-(2-(4-chlorophenyl)ethyl)-4-ethyl-1,3-dioxolan-2-yl]methyl]imidazole-hydrogen oxalate salt, m.p. 133°–135.5° C. By substituting the appropriate ketones for 1-[4-(4-chlorophenyl)butan-2-on-1-yl]imidazole and substituting 1,2-butanediol for ethylene glycol in part (a) of this example the following compounds are prepared:
1-[[2-(2-phenylethyl)-4-ethyl-1,3-dioxolan-2-yl]methyl]imidazole,
1-[[2-(2-(4-fluorophenyl)ethyl)-4-ethyl-1,3-dioxolan-2-yl]methyl]imidazole,
1-[[2-(2-(2-chlorophenyl)ethyl)-4-ethyl-1,3-dioxolan-2-yl]methyl]imidazole,
1-[[2-(2-(3-chlorophenyl)ethyl)-4-ethyl-1,3-dioxolan-2-yl]methyl]imidazole,
1-[[2-(2-(2,4-dichlorophenyl)ethyl-4-ethyl-1,3-dioxolan-2-yl]methyl]imidazole,
1-[[2-(2-(2,4,6-trichlorophenyl)ethyl)-4-ethyl-1,3-dioxolan-2-yl]methyl]imidazole,
1-[[2-(2-(3-methylphenyl)ethyl)-4-ethyl-1,3-dioxolan-2-yl]methyl]imidazole,
1-[[2-(2-(4-methylphenyl)ethyl)-4-ethyl-1,3-dioxolan-2-yl]methyl]imidazole,
1-[[2-(2-(4-i-propylphenyl)ethyl)-4-ethyl-1,3-dioxolan-2-yl]methyl]imidazole,
1-[[2-(2-(4-t-butylphenyl)ethyl)-4-ethyl-1,3-dioxolan-2-yl]methyl]imidazole,
1-[[2-(2-(2,4-dimethylphenyl)ethyl)-4-ethyl-1,3-dioxolan-2-yl]methyl]imidazole,
1-[[2-(2-(3,5-dimethylphenyl)ethyl)-4-ethyl-1,3-dioxolan-2-yl]methyl]imidazole,
1-[[2-(2-(2,4,6-trimethylphenyl)ethyl)-4-ethyl-1,3-dioxolan-2-yl]methyl]imidazole,
1-[[2-(2-(2,3,5,6-tetramethylphenyl)ethyl)-4-ethyl-1,3-dioxolan-2-yl]methyl]imidazole,
1-[[2-(2-(2,3,4,5,6-pentamethylphenyl)ethyl)-4-ethyl-1,3-dioxolan-2-yl]methyl]imidazole,
1-[[2-(2-(3-methoxyphenyl)ethyl)-4-ethyl-1,3-dioxolan-2-yl]methyl]imidazole,
1-[[2-(2-(4-methoxyphenyl)ethyl)-4-ethyl-1,3-dioxolan-2-yl]methyl]imidazole,
1-[[2-(2-(4-n-butoxyphenyl)ethyl)-4-ethyl-1,3-dioxolan-2-yl]methyl]imidazole.

(e) Substituting n-pentane-1,2-diol for ethylene glycol in part (a) in this example there is prepared 1-[[2-(2-(4-chlorophenyl)ethyl)-4-n-propyl-1,3-dioxolan-2-yl]methyl]imidazole. By substituting the appropriate ketones for 1-[4-(4-chlorophenyl)butan-2-on-1-yl]imidazole and substituting n-pentane-1,2-diol for ethylene glycol in part (a) of this example the following compounds are prepared:
1-[[2-(2-phenylethyl)-4-n-propyl-1,3-dioxolan-2-yl]methyl]imidazole,
1-[[2-(2-(4-fluorophenyl)ethyl)-4-n-propyl-1,3-dioxolan-2-yl]methyl]imidazole,
1-[[2-(2-(2-chlorophenyl)ethyl)-4-n-propyl-1,3-dioxolan-2-yl]methyl]imidazole,
1-[[2-(2-(3-chlorophenyl)ethyl-4-n-propyl-1,3-dioxolan-2-yl]methyl]imidazole,
1-[[2-(2-(2,4-dichlorophenyl)ethyl)-4-n-propyl-1,3-dioxolan-2-yl]methyl]imidazole,
1-[[2-(2-(2,4,6-trichlorophenyl)ethyl)-4-n-propyl-1,3-dioxolan-2-yl]methyl]imidazole,
1-[[2-(2-(3-methylphenyl)ethyl)-4-n-propyl-1,3-dioxolan-2-yl]methyl]imidazole,
1-[[2-(2-(4-methylphenyl)ethyl)-4-n-propyl-1,3-dioxolan-2-yl]methyl]imidazole,
1-[[2-(2-(4-i-propylphenyl)ethyl)-4-n-propyl-1,3-dioxolan-2-yl]methyl]imidazole,
1-[[2-(2-(4-t-butylphenyl)ethyl)-4-n-propyl-1,3-dioxolan-2-yl]methyl]imidazole,
1-[[2-(2,4-dimethylphenyl)ethyl)-4-n-propyl-1,3-dioxolan-2-yl]methyl]imidazole,
1-[[2-(2-(3,5-dimethylphenyl)ethyl)-4-n-propyl-1,3-dioxolan-2-yl]methyl]imidazole,
1-[[2-(2-(2,4,6-trimethylphenyl)ethyl)-4-n-propyl-1,3-dioxolan-2-yl]methyl]imidazole,
1-[[2-(2-(2,3,5,6-tetramethylphenyl)ethyl)-4-n-propyl-1,3-dioxolan-2-yl]methyl]imidazole,
1-[[2-(2-(2,3,4,5,6-pentamethylphenyl)ethyl)-4-n-propyl-1,3-dioxolan-2-yl]methyl]imidazole,
1-[[2-(2-(3-methoxyphenyl)ethyl-4-n-propyl-1,3-dioxolan-2-yl]methyl]imidazole,
1-[[2-(2-(4-methoxyphenyl)ethyl)-4-n-propyl-1,3-dioxolan-2-yl]methyl]imidazole,
1-[[2-(2-(4-n-butoxyphenyl)ethyl)-4-n-propyl-1,3-dioxolan-2-yl]methyl]imidazole.

(f) Substituting 3-methylbutane-1,2-diol for ethylene glycol in part (a) of this example there is prepared 1-[[2-(2-(4-chlorophenyl)ethyl)-4-(1-methylethyl)-1,3-dioxolan-2-yl]methyl]imidazole. By substituting the appropriate ketones for 1-[4-(4-chlorophenyl)butan-2-on-1-yl]imidazole and substituting 3-methylbutane-1,2-diol for ethylene glycol in part (a) of this example the following compounds are prepared:
1-[[2-(2-phenylethyl)-4-(1-methylethyl)-1,3-dioxolan-2-yl]methyl]imidazole, 1-[[2-(2-(4-fluorophenyl)ethyl)-4-(1-methylethyl)-1,3-dioxolan-2-yl]methyl]imidazole,
1-[[2-(2-(2-chlorophenyl)ethyl)-4-(1-methylethyl)-1,3-dioxolan-2-yl]methyl]imidazole,
1-[[2-(2-(3-chlorophenyl)ethyl)-4-(1-methylethyl)-1,3-dioxolan-2-yl]methyl]imidazole,
1-[[2-(2-(2,4-dichlorophenyl)ethyl)-4-(1-methylethyl)-1,3-dioxolan-2-yl]methyl]imidazole,
1-[[2-(2-(2,4,6-trichlorophenyl)ethyl)-4-(1-methylethyl)-1,3-dioxolan-2-yl]methyl]imidazole,
1-[[2-(2-(3-methylphenyl)ethyl)-4-(1-methylethyl)-1,3-dioxolan-2-yl]methyl]imidazole,
1-[[2-(2-(4-methylphenyl)ethyl)-4-(1-methylethyl)-1,3-dioxolan-2-yl]methyl]imidazole,
1-[[2-(2-(4-i-propylphenyl)ethyl)-4-(1-methylethyl)-1,3-dioxolan-2-yl]methyl]imidazole,
1-[[2-(2-(4-t-butylphenyl)ethyl)-4-(1-methylethyl)-1,3-dioxolan-2-yl]methyl]imidazole,
1-[[2-(2-(2,4-dimethylphenyl)ethyl)-4-(1-methylethyl)-1,3-dioxolan-2-yl]methyl]imidazole,
1-[[2-(2-(3,5-dimethylphenyl)ethyl)-4-(1-methylethyl)-1,3-dioxolan-2-yl]methyl]imidazole,
1-[[2-(2-(2,4,6-trimethylphenyl)ethyl)-4-(1-methylethyl)-1,3-dioxolan-2-yl]methyl]imidazole,
1-[[2-(2-(2,3,5,6-tetramethylphenyl)ethyl)-4-(1-methylethyl)-1,3-dioxolan-2-yl]methyl]imidazole,
1-[[2-(2-(2,3,4,5,6-pentamethylphenyl)ethyl)-4-(1-methylethyl)-1,3-dioxolan-2-yl]methyl]imidazole,
1-[[2-(2-(3-methoxyphenyl)ethyl)-4-(1-methylethyl)-1,3-dioxolan-2-yl]methyl]imidazole,
1-[[2-(2-(4-methoxyphenyl)ethyl)-4-(1-methylethyl)-1,3-dioxolan-2-yl]methyl]imidazole,
1-[[2-(2-(4-n-butoxyphenyl)ethyl)-4-(1-methylethyl)-1,3-dioxolan-2-yl]methyl]imidazole, (g) Substituting n-hexane-1,2-diol for ethylene glycol in part (a) of this example there is prepared 1-[[2-(2-(4-chlorophenyl)ethyl)-4-n-butyl-1,3-dioxolan-2-yl]methyl]imidazole. By substituting the appropriate ketones for 1-[4-(4-chlorophenyl)butan-2-on-1-yl]imidazole and substituting n-hexane-1,2-diol for ethylene glycol in part (a) of this example the following compounds are prepared:
1-[[2-(2-phenylethyl)-4-n-butyl-1,3-dioxolan-2-yl]methyl]imidazole,
1-[[2-(2-(4-fluorophenyl)ethyl)-4-n-butyl-1,3-dioxolan-2-yl]methyl]imidazole,
1-[[2-(2-(2-chlorophenyl)ethyl)-4-n-butyl-1,3-dioxolan-2-yl]methyl]imidazole,
1-[[2-(2-(3-chlorophenyl)ethyl)-4-n-butyl-1,3-dioxolan-2-yl]methyl]imidazole,
1-[[2-(2-(2,4-dichlorophenyl)ethyl)-4-n-butyl-1,3-dioxolan-2-yl]methyl]imidazole,
1-[[2-(2-(2,4,6-trichlorophenyl)ethyl)-4-n-butyl-1,3-dioxolan-2-yl]methyl]imidazole,
1-[[2-(2-(3-methylphenyl)ethyl)-4-n-butyl-1,3-dioxolan-2-yl]methyl]imidazole,
1-[[2-(2-(4-methylphenyl)ethyl)-4-n-butyl-1,3-dioxolan-2-yl]methyl]imidazole,
1-[[2-(2-(4-i-propylphenyl)ethyl)-4-n-butyl-1,3-dioxolan-2-yl]methyl]imidazole,
1-[[2-(2-(4-t-butylphenyl)ethyl)-4-n-butyl-1,3-dioxolan-2-yl]methyl]imidazole,
1-[[2-(2-(2,4-dimethylphenyl)ethyl)-4-n-butyl-1,3-dioxolan-2-yl]methyl]imidazole,
1-[[2-(2-(3,5-dimethylphenyl)ethyl)-4-n-butyl-1,3-dioxolan-2-yl]methyl]imidazole,
1-[[2-(2-(2,4,6-trimethylphenyl)ethyl)-4-n-butyl-1,3-dioxolan-2-yl]methyl]imidazole,
1-[[2-(2-(2,3,5,6-tetramethylphenyl)ethyl)-4-n-butyl-1,3-dioxolan-2-yl]methyl]imidazole,
1-[[2-(2-(2,3,4,5,6-pentamethylphenyl)ethyl)-4-n-butyl-1,3-dioxolan-2-yl]methyl]imidazole,
1-[[2-(2-(3-methoxyphenyl)ethyl)-4-n-butyl-1,3-dioxolan-2-yl]methyl]imidazole,
1-[[2-(2-(4-methoxyphenyl)ethyl)-4-n-butyl-1,3-dioxolan-2-yl]methyl]imidazole,
1-[[2-(2-(4-n-butoxyphenyl)ethyl)-4-n-butyl-1,3-dioxolan-2-yl]methyl]imidazole.

(h) Substituting 4-methylpentane-1,2-diol for ethylene glycol in part (a) of this example there is prepared 1-[[2-(2-(4-chlorophenyl)ethyl)-4-(2-methylpropyl)-1,3-dioxolan-2-yl]methyl]imidazole. By substituting the appropriate ketones for 1-[4-(4-chlorophenyl)butan-2-on-1-yl]imidazole and substituting 4-methylpentane-1,2-diol for ethylene glycol in part (a) of this example the following compounds are prepared:
1-[[2-(2-phenylethyl)-4-(2-methylpropyl)-1,3-dioxolan-2-yl]methyl]imidazole,
1-[[2-(2-(4-fluorophenyl)ethyl)-4-(2-methylpropyl)-1,3-dioxolan-2-yl]methyl]imidazole,
1-[[2-(2-(2-chlorophenyl)ethyl)-4-(2-methylpropyl)-1,3-dioxolan-2-yl]methyl]imidazole,
1-[[2-(2-(3-chlorophenyl)ethyl-4-(2-methylpropyl)-1,3-dioxolan-2-yl]methyl]imidazole,
1-[[2-(2-(2,4-dichlorophenyl)ethyl)-4-(2-methylpropyl)-1,3-dioxolan-2-yl]methyl]imidazole,
1-[[2-(2-(2,4,6-trichlorophenyl)ethyl)-4-(2-methylpropyl)-1,3-dioxolan-2-yl]methyl]imidazole,
1-[[2-(2-(3-methylphenyl)ethyl)-4-(2-methylpropyl)-1,3-dioxolan-2-yl]methyl]imidazole,
1-[[2-(2-(4-methylphenyl)ethyl)-4-(2-methylpropyl)-1,3-dioxolan-2-yl]methyl]imidazole,
1-[[2-(2-(4-i-propylphenyl)ethyl)-4-(2-methylpropyl)-1,3-dioxolan-2-yl]methyl]imidazole,
1-[[2-(2-(4-t-butylphenyl)ethyl)-4-(2-methylpropyl)-1,3-dioxolan-2-yl]methyl]imidazole,
1-[[2-(2-(2,4-dimethylphenyl)ethyl)-4-(2-methylpropyl)-1,3-dioxolan-2-yl]methyl]imidazole,
1-[[2-(2-(3,5-dimethylphenyl)ethyl)-4-(2-methylpropyl)-1,3-dioxolan-2-yl]methyl]imidazole,
1-[[2-(2-(2,4,6-trimethylphenyl)ethyl)-4-(2-methylpropyl)-1,3-dioxolan-2-yl]methyl]imidazole,
1-[[2-(2-(2,3,5,6-tetramethylphenyl)ethyl)-4-(2-methylpropyl)-1,3-dioxolan-2-yl]methyl]imidazole,
1-[[2-(2-(2,3,4,5,6-pentamethylphenyl)ethyl)-4-(2-methylpropyl)-1,3-dioxolan-2-yl]methyl]imidazole,
1-[[2-(2-(3-methoxyphenyl)ethyl)-4-(2-methylpropyl)-1,3-dioxolan-2-yl]methyl]imidazole,
1-[[2-(2-(4-methoxyphenyl)ethyl)-4-(2-methylpropyl)-1,3-dioxolan-2-yl]methyl]imidazole,
1-[[2-(2-(4-n-butoxyphenyl)ethyl)-4-(2-methylpropyl)-1,3-dioxolan-2-yl]methyl]imidazole.

(i) Substituting 3-methylpentane-1,2-diol for ethylene glycol in part (a) of this example there is prepared 1-[[2-(2-(4-chlorophenyl)ethyl)-4-(1-methylpropyl)-1,3-dioxolan-2-yl]methyl]imidazole. By substituting the appropriate ketones for 1-[4-(4-chlorophenyl)butan-2-on-1-yl]imidazole and substituting 3-methylpentane-1,2-diol for ethylene glycol in part (a) of this example the following compounds are prepared:
1-[[2-(2-phenylethyl)-4-(1-methylpropyl)-1,3-dioxolan-2-yl]methyl]imidazole,
1-[[2-(2-(4-methylphenyl)ethyl)-4-(1-methylpropyl)-1,3-dioxolan-2-yl]methyl]imidazole,
1-[[2-(2-(4-methoxyphenyl)ethyl)-4-(1-methylpropyl)-1,3-dioxolan-2-yl]methyl]imidazole.

(j) Substituting 3,3-dimethylbutane-1,2-diol for ethylene glycol in part (a) of this example there is prepared 1-[[2-(2-(4-chlorophenyl)ethyl)-4-(t-butyl)-1,3-dioxolan-2-yl]methyl]imidazole. By substituting the appropriate ketones for 1-[4-(4-chlorophenyl)butan-2-on-1-yl]imidazole and substituting 3,3-dimethylbutane-1,2-diol for ethylene glycol in part (a) of this example the following compounds are prepared:

1-[[2-(2-phenylethyl)-4-t-butyl-1,3-dioxolan-2-yl]methyl]imidazole,
1-[[2-(2-(4-methylphenyl)ethyl)-4-t-butyl-1,3-dioxolan-2-yl]methyl]imidazole,
1-[[2-(2-(4-methoxyphenyl)ethyl)-4-t-butyl-1,3-dioxolan-2-yl]methyl]imidazole.

(k) Substituting 2,3-butanediol for ethylene glycol in part (a) of this example there is prepared 1-[[2-(2-(4-chlorophenyl)ethyl)-4,5-dimethyl-1,3-dioxolan-2-yl]methyl]imidazole. By substituting the appropriate ketones for 1-[4-(4-chlorophenyl)butan-2-on-1-yl]imidazole and substituting 2,3-butanediol for ethylene glycol in part (a) of this example the following compounds are prepared:

1-[[2-(2-phenylethyl)-4,5-dimethyl-1,3-dioxolan-2-yl]methyl]imidazole,
1-[[2-(2-(4-fluorophenyl)ethyl)-4,5-dimethyl-1,3-dioxolan-2-yl]methyl]imidazole,
1-[[2-(2-(2-chlorophenyl)ethyl)-4,5-dimethyl-1,3-dioxolan-2-yl]methyl]imidazole,
1-[[2-(2-(3-chlorophenyl)ethyl)-4,5-dimethyl-1,3-dioxolan-2-yl]methyl]imidazole,
1-[[2-(2-(2,4-dichlorophenyl)ethyl)-4,5-dimethyl-1,3-dioxolan-2-yl]methyl]imidazole,
1-[[2-(2-(2,4,6-trichlorophenyl)ethyl)-4,5-dimethyl-1,3-dioxolan-2-yl]methyl]imidazole,
1-[[2-(2-(3-methylphenyl)ethyl)-4,5-dimethyl-1,3-dioxolan-2-yl]methyl]imidazole,
1-[[2-(2-(4-methylphenyl)ethyl)-4,5-dimethyl-1,3-dioxolan-2-yl]methyl]imidazole,
1-[[2-(2-(4-i-propylphenyl)ethyl)-4,5-dimethyl-1,3-dioxolan-2-yl]methyl]imidazole,
1-[[2-(2-(4-t-butylphenyl)ethyl)-4,5-dimethyl-1,3-dioxolan-2-yl]methyl]imidazole,
1-[[2-(2-(2,4-dimethylphenyl)ethyl)-4,5-dimethyl-1,3-dioxolan-2-yl]methyl]imidazole,
1-[[2-(2-(3,5-dimethylphenyl)ethyl)-4,5-dimethyl-1,3-dioxolan-2-yl]methyl]imidazole,
1-[[2-(2-(2,4,6-trimethylphenyl)ethyl)-4,5-dimethyl-1,3-dioxolan-2-yl]methyl]imidazole,
1-[[2-(2-(2,3,5,6-tetramethylphenyl)ethyl)-4,5-dimethyl-1,3-dioxolan-2-yl]methyl]imidazole,
1-[[2-(2-(2,3,4,5,6-pentamethylphenyl)ethyl)-4,5-dimethyl-1,3-dioxolan-2-yl]methyl]imidazole,
1-[[2-(2-(3-methoxyphenyl)ethyl)-4,5-dimethyl-1,3-dioxolan-2-yl]methyl]imidazole,
1-[[2-(2-(4-methoxyphenyl)ethyl)-4,5-dimethyl-1,3-dioxolan-2-yl]methyl]imidazole,
1-[[2-(2-(4-n-butoxyphenyl)ethyl)-4,5-dimethyl-1,3-dioxolan-2-yl]methyl]imidazole.

EXAMPLE 2

(a) A mixture of 1-[4-(4-chlorophenyl)butan-2-on-1-yl]imidazole (2.0 g), 2,2-dimethylpropane-1,3-diol (0.84 g) and anhydrous p-toluenesulfonic acid (1.39 g) in toluene (20 ml) were heated under reflux through a Dean-Stark trap for 2 hours. The resulting mixture was poured into aqueous potassium carbonate solution, extracted with ether (2×100 ml) and the extracts dried (MgSO$_4$). After removal of the solvent, the crude reaction product was chromatographed on silica gel eluting with 7% methanol in methylene chloride to give 1-[[2-(2-(4-chlorophenyl)ethyl)-5,5-dimethyl-1,3-dioxan-2-yl]methyl]imidazole (1.0 g) as a colorless oil which crystallized. The oil was dissolved in ether, the solution filtered and the hydrochloride salt formed by dropwise addition of ethereal hydrogen chloride until precipitation was almost complete. The precipitate was filtered, washed with ether and dried in vacuo to give 1-[[2-(2-(4-chlorophenyl)ethyl)-5,5-dimethyl-1,3-dioxan-2-yl]methyl]imidazole hydrochloride, m.p. 190°–191° C.

In parts (b) through (1) of this example, where indicated, the compounds are further characterized by conversion to the indicated acid addition salt.

(b) Substituting the appropriate ketones for 1-[4-(4-chlorophenyl)butan-2-on-1-yl]imidazole in part (a) of this example the following compounds are prepared:

1-[[2-(2-phenylethyl)-5,5-dimethyl-1,3-dioxan-2-yl]methyl]imidazole-hydrobromide salt, m.p. 171°–173° C.,
1-[[2-(2-(4-fluorophenyl)ethyl)-5,5-dimethyl-1,3-dioxan-2-yl]methyl]imidazole,
1-[[2-(2-(2-chlorophenyl)ethyl)-5,5-dimethyl-1,3-dioxan-2-yl]methyl]imidazole,
1-[[2-(2-(3-chlorophenyl)ethyl)-5,5-dimethyl-1,3-dioxan-2-yl]methyl]imidazole,
1-[[2-(2-(2,4-dichlorophenyl)ethyl)-5,5-dimethyl-1,3-dioxan-2-yl]methyl]imidazole,
1-[[2-(2-(2,4,6-trichlorophenyl)ethyl)-5,5,-dimethyl-1,3-dioxan-2-yl]methyl]imidazole,
1-[[2-(2-(3-methylphenyl)ethyl)-5,5-dimethyl-1,3-dioxan-2-yl]methyl]imidazole,
1-[[2-(2-(4-methylphenyl)ethyl)-5,5-dimethyl-1,3-dioxan-2-yl]methyl]imidazole,
1-[[2-(2-(4-i-propylphenyl)ethyl)-5,5-dimethyl-1,3-dioxan-2-yl]methyl]imidazole,
1-[[2-(2-(4-t-butylphenyl)ethyl-5,5-dimethyl-1,3-dioxan-2-yl]methyl]imidazole,
1-[[2-(2-(2,4-dimethylphenyl)ethyl)-5,5-dimethyl-1,3-dioxan-2-yl]methyl]imidazole,
1-[[2-(2-(3,5-dimethylphenyl)ethyl)-5,5-dimethyl-1,3-dioxan-2-yl]methyl]imidazole,
1-[[2-(2-(2,4,6-trimethylphenyl)ethyl)-5,5-dimethyl-1,3-dioxan-2-yl]methyl]imidazole,
1-[[2-(2-(2,3,5,6-tetramethylphenyl)ethyl)-5,5-dimethyl-1,3-dioxan-2-yl]methyl]imidazole,
1-[[2-(2-(2,3,4,5,6-pentamethylphenyl)ethyl)-5,5-dimethyl-1,3-dioxan-2-yl]methyl]imidazole,
1-[[2-(2-(3-methoxyphenyl)ethyl)-5,5-dimethyl-1,3-dioxan-2-yl]methyl]imidazole,
1-[[2-(2-(4-methoxyphenyl)ethyl)-5,5-dimethyl-1,3-dioxan-2-yl]methyl]imidazole,
1-[[2-(2-(4-n-butoxyphenyl)ethyl)-5,5-dimethyl-1,3-dioxan-2-yl]methyl]imidazole,
1-[2-(2-benzyl-5,5-dimethyl-1,3-dioxan-2-yl)ethyl]imidazole,
1-[2-(2-(4-chlorobenzyl)-5,5-dimethyl-1,3-dioxan-2-yl)ethyl]imidazole,
1-[2-(2-(4-bromobenzyl)-5,5-dimethyl-1,3-dioxan-2-yl)ethyl]imidazole,
1-[2-(2-(2,4-dichlorobenzyl)-5,5-dimethyl-1,3-dioxan-2-yl)ethyl]imidazole,
1-[2-(2-(3-methylbenzyl)-5,5-dimethyl-1,3-dioxan-2-yl)ethyl]imidazole,
1-[2-(2-(4-methylbenzyl)-5,5-dimethyl-1,3-dioxan-2-yl)ethyl]imidazole,
1-[2-(2-(4-t-butylbenzyl)-5,5-dimethyl-1,3-dioxan-2-yl)ethyl]imidazole, 1-[2-(2-(2,4-dimethylbenzyl)-5,5-dimethyl-1,3-dioxan-2-yl)ethyl]imidazole,
1-[2-(2-(3,5-dimethylbenzyl)-5,5-dimethyl-1,3-dioxan-2-yl)ethyl]imidazole,
1-[2-(2-(2,4,6-trimethylbenzyl)-5,5-dimethyl-1,3-dioxan-2-yl)ethyl]imidazole,
1-[2-(2-(2,3,5,6-tetramethylbenzyl)-5,5-dimethyl-1,3-dioxan-2-yl)ethyl]imidazole,
1-2-(2-(2,3,4,5,6-pentamethylbenzyl)-5,5-dimethyl-1,3-dioxan-2-yl)ethyl]imidazole,
1-[2-(2-(3-methoxybenzyl)-5,5-dimethyl-1,3-dioxan-2-yl)ethyl]imidazole,
1-[2-(2-(4-methoxybenzyl)-5,5-dimethyl-1,3-dioxan-2-yl)ethyl]imidazole,
1-[2-(2-(4-n-butoxybenzyl)-5,5-dimethyl-1,3-dioxan-2-yl)ethyl]imidazole,
1-[[2-benzyl-5,5-dimethyl-1,3-dioxan-2-yl]methyl]imidazole,
1-[[2-(4-chlorobenzyl)-5,5-dimethyl-1,3-dioxan-2-yl]methyl]imidazole-hydrogen oxalate salt, m.p. 183°–184° C.,
1-[[2-(3-methylbenzyl)-5,5-dimethyl-1,3-dioxan-2-yl]methyl]imidazole,
1-[[2-(4-methylbenzyl)-5,5-dimethyl-1,3-dioxan-2-yl]methyl]imidazole,
1-[[2-(4-i-propylbenzyl)-5,5-dimethyl-1,3-dioxan-2-yl]methyl]imidazole,
1-[[2-(4-t-butylphenyl)-5,5-dimethyl-1,3-dioxan-2-yl]methyl]imidazole,
1-[[2-(2,4-dimethylbenzyl)-5,5-dimethyl-1,3-dioxan-2-yl]methyl]imidazole,
1-[[2-(3,5-dimethylbenzyl)-5,5-dimethyl-1,3-dioxan-2-yl]methyl]imidazole,
1-[[2-(2,4,6-trimethylbenzyl)-5,5-dimethyl-1,3-dioxan-2-yl]methyl]imidazole,
1-[[2-(2,3,5,6-tetramethylbenzyl)-5,5-dimethyl-1,3-dioxan-2-yl]methyl]imidazole,
1-[[2-(2,3,4,5,6-pentamethylbenzyl)-5,5-dimethyl-1,3-dioxan-2-yl]methyl]imidazole,
1-[[2-(3-methoxybenzyl)-5,5-dimethyl-1,3-dioxan-2-yl]methyl]imidazole,
1-[[2-(4-methoxybenzyl)-5,5-dimethyl-1,3-dioxan-2-yl]methyl]imidazole,
1-[[2-(4-t-butoxybenzyl)-5,5-dimethyl-1,3-dioxan-2-yl]methyl]imidazole,
1-[[2-(3-phenylpropyl)-5,5-dimethyl-1,3-dioxan-2-yl]methyl]imidazole,
1-[[2-(3-(4-methylphenyl)propyl)-5,5-dimethyl-1,3-dioxan-2-yl]methyl]imidazole,
1-[[2-(3-(4-chlorophenyl)propyl)-5,5-dimethyl-1,3-dioxan-2-yl]methyl]imidazole,
1-[[2-(3-(4-methoxyphenyl)propyl)-5,5-dimethyl-1,3-dioxan-2-yl]methyl]imidazole,
1-[2-[2-(2-phenylethyl)-5,5-dimethyl-1,3-dioxan-2-yl]ethyl]imidazole,
1-[2-[2-(4-methylphenyl)ethyl)-5,5-dimethyl-1,3-dioxan-2-yl]ethyl]imidazole,
1-[2-[2-(4-chlorophenyl)ethyl)-5,5-dimethyl-1,3-dioxan-2-yl]ethyl]imidazole,
1-[2-[2-(4-methoxyphenyl)ethyl)-5,5-dimethyl-1,3-dioxan-2-yl]ethyl]imidazole,
1-[3-(2-benzyl-5,5-dimethyl-1,3-dioxan-2-yl)-n-propyl]imidazole,
1-[3-(2-(4-methylbenzyl)-5,5-dimethyl-1,3-dioxan-2-yl)-n-propyl]imidazole,
1-[3-(2-(4-chlorobenzyl)-5,5-dimethyl-1,3-dioxan-2-yl)-n-propyl]imidazole,
1-[3-(2-(4-methoxybenzyl)-5,5-dimethyl-1,3-dioxan-2-yl)-n-propyl]imidazole.

(c) Substituting propane-1,3-diol for 2,2-dimethylpropane-1,3-diol in part (a) of this example there is obtained 1-[[2-(2-(4-chlorophenyl)ethyl)-1,3-dioxan-2-yl]methyl]imidazole. By substituting the appropriate ketones for 1-[4-(4-chlorophenyl)butan-2-on-1-yl]imidazole and substituting propane-1,3-diol for 2,2-dimethylpropane-1,3-diol in part (a) of this example the following compounds are prepared:

1-[[2-(2-phenylethyl)-1,3-dioxan-2-yl]methyl]imidazole-hydrochloride salt, m.p. 206°–207° C.,
1-[[2-(2-(4-fluorophenyl)ethyl)-1,3-dioxan-2-yl]methyl]imidazole,
1-[[2-(2-(2-chlorophenyl)ethyl)-1,3-dioxan-2-yl]methyl]imidazole,
1-[[2-(2-(3-chlorophenyl)ethyl)-1,3-dioxan-2-yl]methyl]imidazole,
1-[[2-(2-(2,4-dichlorophenyl)ethyl-1,3-dioxan-2-yl]methyl]imidazole,
1-[[2-(2-(2,4,6-trichlorophenyl)ethyl)-1,3-dioxan-2-yl]methyl]imidazole,
1-[[2-(2-(3-methylphenyl)ethyl)-1,3-dioxan-2-yl]methyl]imidazole,
1-[[2-(2-(4-methylphenyl)ethyl)-1,3-dioxan-2-yl]methyl]imidazole-hydrobromide salt, m.p. 209.5°–211° C.,
1-[[2-(2-(4-i-propylphenyl)ethyl)-1,3-dioxan-2-yl]methyl]imidazole,
1-[[2-(2-(4-t-butylphenyl)ethyl)-1,3-dioxan-2-yl]methyl]imidazole,
1-[[2-(2-(2,4-dimethylphenyl)ethyl)-1,3-dioxan-2-yl]methyl]imidazole,
1-[[2-(2-(2,4,6-trimethylphenyl)ethyl)-1,3-dioxan-2-yl]methyl]imidazole,
1-[[2-(2-(3,5-dimethylphenyl)ethyl)-1,3-dioxan-2-yl]methyl]imidazole,
1-[[2-(2-(2,3,5,6-tetramethylphenyl)ethyl)-1,3-dioxan-2-yl]methyl]imidazole,
1-[[2-(2-(2,3,4,5,6-pentamethylphenyl)ethyl)-1,3-dioxan-2-yl]methyl]imidazole,
1-[[2-(2-(3-methoxyphenyl)ethyl)-1,3-dioxan-2-yl]methyl]imidazole,
1-[[2-(2-(4-methoxyphenyl)ethyl)-1,3-dioxan-2-yl]methyl]imidazole,
1-[[2-(2-(4-n-butoxyphenyl)ethyl)-1,3-dioxan-2-yl]methyl]imidazole,
1-[2-(2-benzyl-1,3-dioxan-2-yl)ethyl]imidazole,
1-[2-(2-(4-chlorobenzyl)-1,3-dioxan-2-yl)ethyl]imidazole,
1-[2-(2-(4-bromobenzyl)-1,3-dioxan-2-yl)ethyl]imidazole,
1-[2-(2-(2,4-dichlorobenzyl)-1,3-dioxan-2-yl)ethyl]imidazole,
1-[2-(2-(3-methylbenzyl)-1,3-dioxan-2-yl)ethyl]imidazole,
1-[2-(2-(4-methylbenzyl)-1,3-dioxan-2-yl)ethyl]imidazole,
1-[2-(2-(4-t-butylbenzyl)-1,3-dioxan-2-yl)ethyl]imidazole,
1-[2-(2-(2,4-dimethylbenzyl)-1,3-dioxan-2-yl)ethyl]imidazole,
1-[2-(2-(3,5-dimethylbenzyl)-1,3-dioxan-2-yl)ethyl]imidazole,
1-[2-(2-(2,4,6-trimethylbenzyl)-1,3-dioxan-2-yl)ethyl]imidazole,
1-[2-(2-(2,3,5,6-tetramethylbenzyl)-1,3-dioxan-2-yl)ethyl]imidazole, 1-[2-(2-(2,3,4,5,6-pentamethylbenzyl)-1,3-dioxan-2-yl)ethyl]imidazole,
1-[2-(2-(3-methoxybenzyl)-1,3-dioxan-2-yl)ethyl]imidazole,
1-[2-(2-(4-methoxybenzyl)-1,3-dioxan-2-yl)ethyl]imidazole,
1-[2-(2-(4-n-butoxybenzyl)-1,3-dioxan-2-yl)ethyl]imidazole,
1-[[2-benzyl-1,3-dioxan-2-yl]methyl]imidazole,
1-[[2-(4-chlorobenzyl)-1,3-dioxan-2-yl]methyl]imidazole,
1-[[2-(3-methylbenzyl)-1,3-dioxan-2-yl]methyl]imidazole,
1-[[2-(4-methylbenzyl)-1,3-dioxan-2-yl]methyl]imidazole-hydrobromide salt, m.p. 193°–196° C.,
1-[[2-(4-i-propylbenzyl)-1,3-dioxan-2-yl]methyl]imidazole,
1-[[2-(4-t-butylbenzyl)-1,3-dioxan-2-yl]methyl]imidazole,
1-[[2-(2,4-dimethylbenzyl)-1,3-dioxan-2-yl]methyl]imidazole,
1-[[2-(3,5-dimethylbenzyl)-1,3-dioxan-2-yl]methyl]imidazole,
1-[[2-(2,4,6-trimethylbenzyl)-1,3-dioxan-2-yl]methyl]imidazole,
1-[[2-(2,3,5,6-tetramethylbenzyl)-1,3-dioxan-2-yl]methyl]imidazole,
1-[[2-(2,3,4,5,6-pentamethylbenzyl)-1,3-dioxan-2-yl]methyl]imidazole,
1-[[2-(3-methoxybenzyl)-1,3-dioxan-2-yl]methyl]imidazole,
1-[[2-(4-methoxybenzyl)-1,3-dioxan-2-yl]methyl]imidazole,
1-[[2-(4-t-butoxybenzyl)-1,3-dioxan-2-yl]methyl]imidazole,
1-[[2-(3-phenylpropyl)-1,3-dioxan-2-yl]methyl]imidazole,
1-[[2-(3-(4-methylphenyl)propyl)-1,3-dioxan-2-yl]methyl]imidazole,
1-[[2-(3-(4-chlorophenyl)propyl)-1,3-dioxan-2-yl]methyl]imidazole,
1-[[2-(3-(4-methoxyphenyl)propyl)-1,3-dioxan-2-yl]methyl]imidazole,
1-[2-[2-(2-phenylethyl)-1,3-dioxan-2-yl]ethyl]imidazole,
1-[2-[2-(2-(4-methylphenyl)ethyl)-1,3-dioxan-2-yl]ethyl]imidazole,
1-[2-[2-(2-(4-chlorophenyl)ethyl)-1,3-dioxan-2-yl]ethyl]imidazole,
1-[2-[2-(2-(4-methoxyphenyl)ethyl)-1,3-dioxan-2-yl]ethyl]imidazole,
1-[3-(2-benzyl-1,3-dioxan-2-yl)-n-propyl]imidazole,
1-[3-(2-(4-methylbenzyl)-1,3-dioxan-2-yl)-n-propyl]imidazole,
1-[3-(2-(4-chlorobenzyl)-1,3-dioxan-2-yl)-n-propyl]imidazole,
1-[3-(2-(4-methoxybenzyl)-1,3-dioxan-2-yl)-n-propyl]imidazole, (d) Substituting 2,2-diethylpropane-1,3-diol for 2,2-dimethylpropane-1,3-diol in part (a) of this example, there is obtained 1-[[2-(2-(4-chlorophenyl)ethyl)-5,5-diethyl-1,3-dioxan-2-yl]methyl]imidazole. By substituting the appropriate ketones for 1-[4-(4-chlorophenyl)-butan-2-on-1-yl]imidazole and substituting 2,2-diethylpropane-1,3-diol for 2,2-dimethylpropane-1,3-diol in part (a) of this example the following compounds are prepared:
1-[[2-(2-phenylethyl)-5,5-diethyl-1,3-dioxan-2-yl]methyl]imidazole,
1-[[2-(2-(4-fluorophenyl)ethyl)-5,5-diethyl-1,3-dioxan-2-yl]methyl]imidazole,
1-[[2-(2-(2-chlorophenyl)ethyl)-5,5-diethyl-1,3-dioxan-2-yl]methyl]imidazole,
1-[[2-(2-(3-chlorophenyl)ethyl)-5,5-diethyl-1,3-dioxan-2-yl]methyl]imidazole,
1-[[2-(2-(2,4-dichlorophenyl)ethyl)-5,5-diethyl-1,3-dioxan-2-yl]methyl]imidazole,
1-[[2-(2-(2,4,6-trichlorophenyl)ethyl)-5,5-diethyl-1,3-dioxan-2-yl]methyl]imidazole,
1-[[2-(2-(3-methylphenyl)ethyl)-5,5-diethyl-1,3-dioxan-2-yl]methyl]imidazole,
1-[[2-(2-(4-methylphenyl)ethyl)-5,5-diethyl-1,3-dioxan-2-yl]methyl]imidazole,
1-[[2-(2-(4-i-propylphenyl)ethyl)-5,5-diethyl-1,3-dioxan-2-yl]methyl]imidazole,
1-[[2-(2-(4-t-butylphenyl)ethyl)-5,5-diethyl-1,3-dioxan-2-yl]methyl]imidazole,
1-[[2-(2-(2,4-dimethylphenyl)ethyl)-5,5-diethyl-1,3-dioxan-2-yl]methyl]imidazole,
1-[[2-(2-(3,5-dimethylphenyl)ethyl)-5,5-diethyl-1,3-dioxan-2-yl]methyl]imidazole,
1-[[2-(2-(2,4,6-trimethylphenyl)ethyl)-5,5-diethyl-1,3-dioxan-2-yl]methyl]imidazole,
1-[[2-(2-(2,3,5,6-tetramethylphenyl)ethyl)-5,5-diethyl-1,3-dioxan-2-yl]methyl]imidazole,
1-[[2-(2-(2,3,4,5,6-pentamethylphenyl)ethyl)-5,5-diethyl-1,3-dioxan-2-yl]methyl]imidazole,
1-[[2-(2-(3-methoxyphenyl)ethyl)-5,5-diethyl-1,3-dioxan-2-yl]methyl]imidazole,
1-[[2-(2-(4-methoxyphenyl)ethyl)-5,5-diethyl-1,3-dioxan-2-yl]methyl]imidazole,
1-[[2-(2-(4-n-butoxyphenyl)ethyl)-5,5-diethyl-1,3-dioxan-2-yl]methyl]imidazole,
1-[2-(2-benzyl-5,5-diethyl-1,3-dioxan-2-yl)ethyl]imidazole,
1-[2-(2-(4-chlorobenzyl)-5,5-diethyl-1,3-dioxan-2-yl)ethyl]imidazole,
1-[2-(2-(4-bromobenzyl)-5,5-diethyl-1,3-dioxan-2-yl)ethyl]imidazole,
1-[2-(2-(2,4-dichlorobenzyl)-5,5-diethyl-1,3-dioxan-2-yl)ethyl]imidazole,
1-[2-(2-(3-methylbenzyl)-5,5-diethyl-1,3-dioxan-2-yl)ethyl]imidazole,
1-[2-(2-(4-methylbenzyl)-5,5-diethyl-1,3-dioxan-2-yl)ethyl]imidazole,
1-[2-(2-(4-t-butylbenzyl)-5,5-diethyl-1,3-dioxan-2-yl)ethyl]imidazole,
1-[2-(2-(2,4-dimethylbenzyl)-5,5-diethyl-1,3-dioxan-2-yl)ethyl]imidazole,
1-[2-(2-(3,5-dimethylbenzyl)-5,5-dimethyl-1,3-dioxan-2-yl)ethyl]imidazole,
1-[2-(2-(2,4,6-trimethylbenzyl)-5,5-diethyl-1,3-dioxan-2-yl)ethyl]imidazole,
1-[2-(2-(2,3,5,6-tetramethylbenzyl)-5,5-diethyl-1,3-dioxan-2-yl)ethyl]imidazole,
1-[2-(2,3,4,5,6-pentamethylbenzyl)-5,5-diethyl-1,3-dioxan-2-yl]imidazole,
1-[2-(3-methoxybenzyl)-5,5-diethyl-1,3-dioxan-2-yl)ethyl]imidazole,
1-[2-(2-(4-methoxybenzyl)-5,5-diethyl-1,3-dioxan-2-yl)ethyl]imidazole,
1-[2-(2-(4-n-butoxybenzyl)-5,5-diethyl-1,3-dioxan-2-yl)ethyl]imidazole,
1-[[2-benzyl-5,5-diethyl-1,3-dioxan-2-yl]methyl]imidazole,
1-[[2-(4-chlorobenzyl)-5,5-diethyl-1,3-dioxan-2-yl]methyl]imidazole, 1-[[2-(3-methylbenzyl)-5,5-diethyl-1,3-dioxan-2-yl]methyl]imidazole,
1-[[2-(4-methylbenzyl)-5,5-diethyl-1,3-dioxan-2-yl]methyl]imidazole,
1-[[2-(4-i-propylbenzyl)-5,5-diethyl-1,3-dioxan-2-yl]methyl]imidazole,
1-[[2-(4-t-butylbenzyl)-5,5-diethyl-1,3-dioxan-2-yl]methyl]imidazole,
1-[[2-(2,4-dimethylbenzyl)-5,5-diethyl-1,3-dioxan-2-yl]methyl]imidazole,
1-[[2-(3,5-dimethylbenzyl)-5,5-diethyl-1,3-dioxan-2-yl]methyl]imidazole,
1-[[2-(2,4,6-trimethylbenzyl)-5,5-diethyl-1,3-dioxan-2-yl]methyl]imidazole,
1-[[2-(2,3,5,6-tetramethylbenzyl)-5,5-diethyl-1,3-dioxan-2-yl]methyl]imidazole,
1-[[2-(2,3,4,5,6-pentabenzyl)-5,5-diethyl-1,3-dioxan-2-yl]methyl]imidazole,
1-[[2-(3-methoxybenzyl)-5,5-diethyl-1,3-dioxan-2-yl]methyl]imidazole,
1-[[2-(4-methoxybenzyl)-5,5-diethyl-1,3-dioxan-2-yl]methyl]imidazole,
1-[[2-(4-t-butoxybenzyl)-5,5-diethyl-1,3-dioxan-2-yl]methyl]imidazole,
1-[[2-(3-phenylpropyl)-5,5-diethyl-1,3-dioxan-2-yl]methyl]imidazole,
1-[[2-(3-(4-methylphenyl)propyl)-5,5-diethyl-1,3-dioxan-2-yl]methyl]imidazole,
1-[[2-(3-(4-chlorophenyl)propyl)-5,5-diethyl-1,3-dioxan-2-yl]methyl]imidazole,
1-[[2-(3-(4-methoxyphenyl)propyl)-5,5-diethyl-1,3-dioxan-2-yl]methyl]imidazole,
1-[2-[2-(2-phenylethyl)-5,5-diethyl-1,3-dioxan-2-yl]ethyl]imidazole,
1-[2-[2-(2-(4-methylphenyl)ethyl)-5,5-diethyl-1,3-dioxan-2-yl]ethyl]imidazole,
1-[2-(2-(2-(4-chlorophenyl)ethyl)-5,5-diethyl-1,3-dioxan-2-yl)ethyl]imidazole,
1-[2-(2-(2-(4-methoxyphenyl)ethyl)-5,5-diethyl-1,3-dioxan-2-yl)ethyl]imidazole,
1-[3-(2-benzyl-5,5-diethyl-1,3-dioxan-2-yl)-n-propyl]imidazole,
1-[3-(2-(4-methylbenzyl)-5,5-diethyl-1,3-dioxan-2-yl)-n-propyl]imidazole,
1-[3-(2-(4-chlorobenzyl)-5,5-diethyl-1,3-dioxan-2-yl)-n-propyl)imidazole,
1-[2-(2-(4-methoxybenzyl)-5,5-diethyl-1,3-dioxane-2-yl)-n-propyl]imidazole.

(e) Substituting 2,2-di-n-propylpropane-1,3-diol for 2,2-dimethylpropane-1,3-diol in part (a) of this example there is obtained 1-[[2-(2-(4-chlorophenyl)ethyl)-5,5-di-n-propyl-1,3-dioxan-2-yl]methyl]imidazole. By substituting the appropriate ketones for 1-[4-(4-chlorophenyl)butan-2-on-1-yl]imidazole and substituting 2,2-di-n-propylpropan-1,3-diol for 2,2-dimethylpropane-1,3-diol in part (a) of this example the following compounds are prepared:

1-[[2-(2-phenylethyl)-5,5-di-n-propyl-1,3-dioxan-2-yl]methyl]imidazole,
1-[[2-(2-(4-fluorophenyl)ethyl)-5,5-di-n-propyl-1,3-dioxan-2-yl]methyl]imidazole,
1-[[2-(2-(2-chlorophenyl)ethyl)-5,5-di-n-propyl-1,3-dioxan-2-yl]methyl]imidazole,
1-[[2-(2-(3-chlorophenyl)ethyl)-5,5-di-n-propyl-1,3-dioxan-2-yl]methyl]imidazole,
1-[[2-(2-(2,4-dichlorophenyl)ethyl)-5,5-di-n-propyl-1,3-dioxan-2-yl]methyl]imidazole,
1-[[2-(2-(2,4,6-trichlorophenyl)ethyl)-5,5-di-n-propyl-1,3-dioxan-2-yl]methyl]imidazole,
1-[[2-(2-(3-methylphenyl)ethyl)-5,5-di-n-propyl-1,3-dioxan-2-yl]methyl]imidazole,
1-[[2-(2-(4-methylphenyl)ethyl)-5,5-di-n-propyl-1,3-dioxan-2-yl]methyl]imidazole,
1-[[2-(2-(4-i-propylphenyl)ethyl)-5,5-di-n-propyl-1,3-dioxan-2-yl]methyl]imidazole,
1-[[2-(2-(4-t-butylphenyl)ethyl)-5,5-di-n-propyl-1,3-dioxan-2-yl]methyl]imidazole,
1-[[2-(2-(2,4-dimethylphenyl)ethyl)-5,5-di-n-propyl-1,3-dioxan-2-yl]methyl]imidazole,
1-[[2-(2-(3,5-dimethylphenyl)ethyl)-5,5-di-n-propyl-1,3-dioxan-2-yl]methyl]imidazole,
1-[[2-(2-(2,4,6-trimethylphenyl)ethyl)-5,5-di-n-propyl-1,3-dioxan-2-yl]methyl]imidazole,
1-[[2-(2-(2,3,5,6-tetramethylphenyl)ethyl)-5,5-di-n-propyl-1,3-dioxan-2-yl]methyl]imidazole,
1-[[2-(2-(2,3,4,5,6-pentamethylphenyl)ethyl)-5,5-di-n-propyl-1,3-dioxan-2-yl]methyl]imidazole,
1-[[2-(2-(3-methoxyphenyl)ethyl)-5,5-di-n-propyl-1,3-dioxan-2-yl]methyl]imidazole,
1-[[2-(2-(4-methoxyphenyl)ethyl)-5,5-di-n-propyl-1,3-dioxan-2-yl]methyl]imidazole,
1-[[2-(2-(4-n-butoxyphenyl)ethyl)-5,5-di-n-propyl-1,3-dioxan-2-yl]methyl]imidazole,
1-[2-(2-benzyl-5,5-di-n-propyl-1,3-dioxan-2-yl)-ethyl]imidazole,
1-[2-(2-(4-chlorobenzyl)-5,5-di-n-propyl-1,3-dioxan-2-yl)ethyl]imidazole,
1-[2-(2-(4-bromobenzyl)-5,5-di-n-propyl-1,3-dioxan-2-yl)ethyl]imidazole,
1-[2-(2-(2,4-dichlorobenzyl)-5,5-di-n-propyl-1,3-dioxan-2-yl)ethyl]imidazole,
1-[2-(2-(3-methylbenzyl)-5,5-di-n-propyl-1,3-dioxan-2-yl)ethyl]imidazole,
1-[2-(2-(4-methylbenzyl)-5,5-di-n-propyl-1,3-dioxan-2-yl)ethyl]imidazole,
1-[2-(2-(4-t-butylbenzyl)-5,5-di-n-propyl-1,3-dioxan-2-yl)ethyl]imidazole,
1-[2-(2-(2,4-dimethylbenzyl)-5,5-di-n-propyl-1,3-dioxan-2-yl)ethyl]imidazole,
1-[2-(2-(3,5-dimethylbenzyl)-5,5-di-n-propyl-1,3-dioxan-2-yl)ethyl]imidazole,
1-[2-(2-(2,4,6-trimethylbenzyl)-5,5-di-n-propyl-1,3-dioxan-2-yl)ethyl]imidazole,
1-[2-(2-(2,3,5,6-tetramethylbenzyl)-5,5-di-n-propyl-1,3-dioxan-2-yl)ethyl]imidazole,
1-[2-(2-(2,3,4,5,6-pentamethylbenzyl)-5,5-di-n-propyl-1,3-dioxan-2-yl)ethyl]imidazole,
1-[2-(2-(3-methoxybenzyl)-5,5-di-n-propyl-1,3-dioxan-2-yl)ethyl]imidazole,
1-[2-(2-(4-methoxybenzyl)-5,5-di-n-propyl-1,3-dioxan-2-yl)ethyl]imidazole,
1-[2-(2-(4-n-butoxybenzyl)-5,5-di-n-propyl-1,3-dioxan-2-yl)ethyl]imidazole,
1-[[2-benzyl-5,5-di-n-propyl-1,3-dioxan-2-yl]methyl]imidazole,
1-[[2-(4-chlorobenzyl)-5,5-di-n-propyl-1,3-dioxan-2-yl]methyl]imidazole,
1-[[2-(3-methylbenzyl)-5,5-di-n-propyl-1,3-dioxan-2-yl]methyl]imidazole,
1-[[2-(4-methylbenzyl)-5,5-di-n-propyl-1,3-dioxan-2-yl]methyl]imidazole,
1-[[2-(4-i-propylbenzyl)-5,5-di-n-propyl-1,3-dioxan-2-yl]methyl]imidazole,
1-[[2-(4-t-butylbenzyl)-5,5-di-n-propyl-1,3-dioxan-2-yl]methyl]imidazole, 1-[[2-(2,4-dimethylbenzyl)-5,5-di-n-propyl-1,3-dioxan-2-yl]methyl]imidazole,
1-[[2-(3,5-dimethylbenzyl)-5,5-di-n-propyl-1,3-dioxan-2-yl]methyl]imidazole,
1-[[2-(2,4,6-trimethylbenzyl)-5,5-di-n-propyl-1,3-dioxan-2-yl]methyl]imidazole,
1-[[2-(2,3,5,6-tetramethylbenzyl)-5,5-di-n-propyl-1,3-dioxan-2-yl]methyl]imidazole,
1-[[2-(2,3,4,5,6-pentamethylbenzyl)-5,5-di-n-propyl-1,3-dioxan-2-yl]methyl]imidazole,
1-[[2-(3-methoxybenzyl)-5,5-di-n-propyl-1,3-dioxan-2-yl]methyl]imidazole,
1-[[2-(4-methoxybenzyl)-5,5-di-n-propyl-1,3-dioxan-2-yl]methyl]imidazole,
1-[[2-(4-t-butoxybenzyl)-5,5-di-n-propyl-1,3-dioxan-2-yl]methyl]imidazole, (f) Substituting 2,2-di(1-methylethyl)propane-1,3-diol for 2,2-dimethylpropane-1,3-diol in part (a) of this example there is obtained 1-[[2-(2-(4-chlorophenyl)ethyl)-5,5-di(1-methylethyl)-1,3-dioxan-2-yl]methyl]imidazole. By substituting the appropriate ketones for 1-[4-(4-chlorophenyl)butan-2-on-1-yl]imidazole and substituting 2,2-di(1-methylethyl)propane-1,3-diol for 2,2-dimethylpropane-1,3-diol in part (a) of this example the following compounds are prepared:
1-[[2-(2-phenylethyl)-5,5-di(1-methylethyl)-1,3-dioxan-2-yl]methyl]imidazole,
1-[[2-(2-(4-methylphenyl)ethyl)-5,5-di(1-methylethyl)-1,3-dioxan-2-yl]methyl]imidazole,
1-[[2-(2-(4-methoxyphenyl)ethyl)-5,5-di(1-methylethyl)-1,3-dioxan-2-yl]methyl]imidazole.

(g) Substituting 2,2-di-n-butylpropane-1,3-diol for 2,2-dimethylpropane-1,3-diol in part (a) of this example there is obtained 1-[[2-(2-(4-chlorophenyl)ethyl)-5,5-di-n-butyl-1,3-dioxan-2-yl]methyl]imidazole. By substituting the appropriate ketones for 1-[4-(4-chlorophenyl)-butan-2-on-1-yl]imidazole and substituting 2,2-di-n-butylpropane-1,3-diol for 2,2-dimethylpropane-1,3-diol in part (a) of this example the following compounds are prepared:
1-[[2-(2-phenylethyl)-5,5-di-n-butyl-1,3-dioxan-2-yl]methyl]imidazole,
1-[[2-(2-(4-methylphenyl)ethyl)-5,5-di-n-butyl-1,3-dioxan-2-yl]methyl]imidazole,
1-[[2-(2-(4-methoxyphenyl)ethyl-5,5-di-n-butyl-1,3-dioxan-2-yl]methyl]imidazole, (h) Substituting n-butan-1,3-diol for 2,2-dimethylpropane-1,3-diol in part (a) of this example there is obtained 1-[[2-(2-(4-chlorophenyl)ethyl)-4-methyl-1,3-dioxan-2-yl]methyl]imidazole-hydrobromide salt, m.p. 220.5°–221.5° C. (dec.). By substituting the appropriate ketones for 1-[4-(4-chlorophenyl)butan-2-on-1-yl]imidazole and substituting n-butane-1,3-diol for 2,2-dimethylpropane-1,3-diol in part (a) of this example the following compounds are prepared.
1-[[2-(2-phenylethyl)-4-methyl-1,3-dioxan-2-yl]methyl]imidazole-hydrobromide salt, m.p. 171.5°–173° C.,
1-[[2-(2-(4-fluorophenyl)ethyl)-4-methyl-1,3-dioxan-2-yl]methyl]imidazole,
1-[[2-(2-(2-chlorophenyl)ethyl)-4-methyl-1,3-dioxan-2-yl]methyl]imidazole,
1-[[2-(2-(3-chlorophenyl)ethyl)-4-methyl-1,3-dioxan-2-yl]methyl]imidazole,
1-[[2-(2-(2,4-dichlorophenyl)ethyl)-4-methyl-1,3-dioxan-2-yl]methyl]imidazole,
1-[[2-(2-(2,4,6-trichlorophenyl)ethyl)-4-methyl-1,3-dioxan-2-yl]methyl]imidazole,
1-[[2-(2-(3-methylphenyl)ethyl)-4-methyl-1,3-dioxan-2-yl]methyl]imidazole,
1-[[2-(2-(4-methylphenyl)ethyl)-4-methyl-1,3-dioxan-2-yl]methyl]imidazole,
1-[[2-(2-(4-i-propylphenyl)ethyl)-4-methyl-1,3-dioxan-2-yl]methyl]imidazole,
1-[[2-(2-(4-t-butylphenyl)ethyl)-4-methyl-1,3-dioxan-2-yl]methyl]imidazole,
1-[[2-(2-(2,4-dimethylphenyl)ethyl)-4-methyl-1,3-dioxan-2-yl]methyl]imidazole,
1-[[2-(2-(3,5-dimethylphenyl)ethyl)-4-methyl-1,3-dioxan-2-yl]methyl]imidazole,
1-[[2-(2-(2,4,6-trimethylphenyl)ethyl)-4-methyl-1,3-dioxan-2-yl]methyl]imidazole,
1-[[2-(2-(2,3,5,6-tetramethylphenyl)ethyl)-4-methyl-1,3-dioxan-2-yl]methyl]imidazole,
1-[[2-(2-(2,3,4,5,6-pentamethylphenyl)ethyl)-4-methyl-1,3-dioxan-2-yl]methyl]imidazole,
1-[[2-(2-(3-methoxyphenyl)ethyl)-4-methyl-1,3-dioxan-2-yl]methyl]imidazole,
1-[[2-(2-(4-methoxyphenyl)ethyl)-4-methyl-1,3-dioxan-2-yl]methyl]imidazole,
1-[[2-(2-(4-n-butoxyphenyl)ethyl)-4-methyl-1,3-dioxan-2-yl]methyl]imidazole.

(i) Substituting 2-(1,1-dimethylethyl)propane-1,3-diol for 2,2-dimethylpropane-1,3-diol in part (a) of this example there is obtained 1-[[2-(2-(4-chlorophenyl)ethyl)-5-t-butyl-1,3-dioxan-2-yl]methyl]imidazole. By substituting the appropriate ketones for 1-[4-(4-chlorophenyl)butan-2-on-1-yl]imidazole and substituting 2-(1,1-dimethylethyl)propane-1,3-diol for 2,2-dimethylpropane-1,3-diol in part (a) of this example the following compounds are prepared:
1-[[2-(2-phenylethyl)-5-t-butyl-1,3-dioxan-2-yl]methyl]imidazole,
1-[[2-(2-(4-methylphenyl)ethyl)-5-t-butyl-1,3-dioxan-2-yl]methyl]imidazole,
1-[[2-(2-(4-methoxyphenyl)ethyl)-5-t-butyl-1,3-dioxan-2-yl]methyl]imidazole.

(j) Substituting 2,2-dimethylbutane-1,3-diol for 2,2-dimethylpropane-1,3-diol in part (a) of this example there is obtained 1-[[2-(2-(4-chlorophenyl)ethyl-4,5,5-trimethyl-1,3-dioxan-2-yl]methyl]imidazole. By substituting the appropriate ketones for 1-[4-(4-chlorophenyl)butan-2-on-1-yl]imidazole and substituting 2,2-dimethylbutane-1,3-diol for 2,2-dimethylpropane-1,3-diol in part (a) of this example the following compounds are prepared:
1-[[2-(2-phenylethyl)-4,5,5-trimethyl-1,3-dioxan-2-yl]methyl]imidazole,
1-[[2-(2-(4-methylphenyl)ethyl)-4,5,5-trimethyl-1,3-dioxan-2-yl]methyl]imidazole,
1-[[2-(2-(4-methoxyphenyl)ethyl)-4,5,5-trimethyl-1,3-dioxan-2-yl]methyl]imidazole.

(k) Substituting n-heptane-3,5-diol for 2,2-dimethylpropane-1,3-diol in part (a) of this example there is obtained 1-[[2-(2-(4-chlorophenyl)ethyl)-4,6-diethyl-1,3-dioxan-2-yl]methyl]imidazole. By substituting the appropriate ketones for 1-[4-(4-chlorophenyl)butan-2-on-1-yl]imidazole and substituting n-heptane-3,5-diol for 2,2-dimethylpropane-1,3-diol in part (a) of this example the following compounds are prepared:
1-[[2-(2-phenylethyl)-4,6-diethyl-1,3-dioxan-2-yl]methyl]imidazole,
1-[[2-(2-(4-methylphenyl)ethyl)-4,6-diethyl-1,3-dioxan-2-yl]methyl]imidazole,
1-[[2-(2-(4-methoxyphenyl)ethyl-4,6-diethyl-1,3-dioxan-2-yl]methyl]imidazole.

(l) Substituting 4,4-dimethylpentane-1,3-diol for 2,2-dimethylpropane-1,3-diol in part (a) of this example there is obtained 1-[[2-(2-(4-chlorophenyl)ethyl)-4-t-butyl-1,3-dioxan-2-yl]methyl]imidazole. By substituting the appropriate ketones for 1-[4-(4-chlorophenyl)butan-2-on-1-yl]imidazole and substituting 4,4-dimethylpentane-1,3-diol for 2,2-dimethylpropane-1,3-diol in part (a) of this example the following compounds are prepared:

1-[[2-(2-phenylethyl)-4-t-butyl-1,3-dioxan-2-yl]methyl]imidazole,
1-[[2-(2-(4-methylphenyl)ethyl)-4-t-butyl-1,3-dioxan-2-yl]methyl]imidazole,
1-[[2-(2-(4-methoxyphenyl)ethyl)-4-t-butyl-1,3-dioxan-2-yl]methyl]imidazole.

EXAMPLE 3

(a) A mixture of 2-(2-chloroethyl)-2-(4-chlorophenyl)-1,3-dioxolane (from 2.03 g of β,p-dichloropropiophenone as in Preparation 3) and imidazole (3.5 g) in acetonitrile (5 ml) were heated at 100° for 24 hours and the solvent removed. After addition of water (30 ml) and ether (30 ml) and shaking, a white solid separated and was collected by filtration. Washing with water, ether and drying in air gave 1-[2-(2-(4-chlorophenyl)-1,3-dioxolan-2-yl]ethyl]imidazole. Further product was obtained by separation of the ether layer, washing, drying (MgSO$_4$) and concentrating.

The free base was dissolved in a small volume of hot ethyl acetate, diluted with ether, and the solution treated dropwise with ethereal hydrogen chloride until precipitation was almost complete. Filtration and recrystallization from ethyl acetate/acetone gave 1-[2-(2-(4-chlorophenyl)-1,3-dioxolan-2-yl)ethyl]imidazole hydrochloride double m.p. 92–94, 128.5°–130° C.

(b) Substituting the appropriate halo ketal for 2-(2-chloroethyl)-2-(4-chlorophenyl)-1,3-dioxolane in part (a) of this example the following compounds are prepared:

1-[3-[2-phenyl-1,3-dioxolan-2-yl]-n-propyl]imidazole-hydrogen oxalate salt, m.p. 127.5°–128.5° C.,
1-[3-[2-(2-chlorophenyl)-1,3-dioxolan-2-yl]-n-propyl]imidazole,
1-[3-[2-(4-methylphenyl)-1,3-dioxolan-2-yl]-n-propyl]imidazole,
1-[3-[2-(4-i-propylphenyl)-1,3-dioxolan-1-yl]-n-propyl]imidazole,
1-[3-[2-(4-methoxyphenyl)-1,3-dioxolan-2-yl]-n-propyl]imidazole,
1-[3-[2-(4-t-butoxyphenyl)-1,3-dioxolan-2-yl]-n-propyl]imidazole,
1-[2-(2-phenyl-1,3-dioxolan-2-yl)ethyl]imidazole,
1-[2-(2-(4-fluorophenyl)-1,3-dioxolan-2-yl)ethyl]imidazole-m.p. 130.5°–132.5° C.,
1-[2-(2-(4-methylphenyl)-1,3-dioxolan-2-yl)ethyl]imidazole-hydrogen oxalate salt, m.p. 160.5°–162° C.,
1-[2-(2-(4-t-butylphenyl)-1,3-dioxolan-2-yl)ethyl]imidazole,
1-[2-(2-(4-methoxyphenyl)-1,3-dioxolan-2-yl)ethyl]imidazole,
1-[2-(2-(4-i-propoxyphenyl)-1,3-dioxolan-2-yl)ethyl]imidazole
1-[3-(2-phenyl-4-methyl-1,3-dioxolan-2-yl)-n-propyl]imidazole,
1-[3-(2-(4-chlorophenyl)-4-methyl-1,3-dioxolan-2-yl)-n-propyl]imidazole,
1-[3-(2-(4-methylphenyl)-4-methyl-1,3-dioxolan-2-yl)-n-propyl]imidazole,
1-[3-(2-(4-i-propylphenyl)-4-methyl-1,3-dioxolan-2-yl)-n-propyl]imidazole,
1-[3-(2-(4-methoxyphenyl)-4-methyl-1,3-dioxolan-2-yl)-n-propyl]imidazole,
1-[3-(2-(4-n-propoxyphenyl)-4-methyl-1,3-dioxolan-2-yl)-n-propyl]imidazole,
1-[3-(2-phenyl-4,5-dimethyl-1,3-dioxolan-2-yl)-n-propyl]imidazole,
1-[3-(2-(4-chlorophenyl)-4,5-dimethyl-1,3-dioxolan-2-yl)-n-propyl]imidazole,
1-[3-(2-(4-methylphenyl)-4,5-dimethyl-1,3-dioxolan-2-yl)-n-propyl]imidazole,
1-[3-(2-(4-i-propylphenyl)-4,5-dimethyl-1,3-dioxolan-2-yl)-n-propyl]imidazole,
1-[3-(2-(4-methoxyphenyl)-4,5-dimethyl-1,3-dioxolan-2-yl)-n-propyl]imidazole,
1-[3-(2-(4-n-propoxyphenyl-4,5-dimethyl-1,3-dioxolan-2-yl)-n-propyl]imidazole,
1-[2-(2-phenyl-4-methyl-1,3-dioxolan-2-yl)ethyl]imidazole,
1-[2-(2-(4-chlorophenyl)-4-methyl-1,3-dioxolan-2-yl)ethyl]imidazole,
1-[2-(2-(4-methylphenyl)-4-methyl-1,3-dioxolan-2-yl)ethyl]imidazole,
1-[2-(2-(4-t-butylphenyl)-4-methyl-1,3-dioxolan-2-yl)ethyl]imidazole,
1-[2-(2-(4-methoxyphenyl)-4-methyl-1,3-dioxolan-2-yl)ethyl]imidazole,
1-[2-(2-(4-i-propoxyphenyl)-4-methyl-1,3-dioxolan-2-yl)ethyl]imidazole,
1-[2-(2-phenyl-4,5-dimethyl-1,3-dioxolan-2-yl)ethyl]imidazole,
1-[2-(2-(4-chlorophenyl)-4,5-dimethyl-1,3-dioxolan-2-yl)ethyl]imidazole,
1-[2-(2-(4-methylphenyl)-4,5-dimethyl-1,3-dioxolan-2-yl)ethyl]imidazole,
1-[2-(2-(4-i-propylphenyl)-4,5-dimethyl-1,3-dioxolan-2-yl)ethyl]imidazole,
1-[2-(2-(4-methoxyphenyl)-4,5-dimethyl-1,3-dioxolan-2-yl)ethyl]imidazole,
1-[2-(2-(4-n-propoxyphenyl)-4,5-dimethyl-1,3-dioxolan-2-yl)ethyl]imidazole,
1-[3-(2-phenyl-5,5-dimethyl-1,3-dioxan-2-yl)-n-propyl]imidazole,
1-[3-(2-(4-chlorophenyl)-5,5-dimethyl-1,3-dioxan-2-yl)-n-propyl]imidazole,
1-[3-(2-(4-methylphenyl)-5,5-dimethyl-1,3-dioxan-2-yl)-n-propyl]imidazole,
1-[3-(2-(4-i-propylphenyl)-5,5-dimethyl-1,3-dioxan-2-yl)-n-propyl]imidazole,
1-[3-(2-(4-methoxyphenyl)-5,5-dimethyl-1,3-dioxan-2-yl)-n-propyl]imidazole,
1-[3-(2-(4-n-propoxyphenyl)-5,5-dimethyl-1,3-dioxan-2-yl)-n-propyl]imidazole,
1-[2-(2-phenyl-5,5-dimethyl-1,3-dioxan-2-yl)ethyl]imidazole,
1-[2-(2-(4-chlorophenyl)-5,5-dimethyl-1,3-dioxan-2-yl)ethyl]imidazole,
1-[2-(2-(4-methylphenyl)-5,5-dimethyl-1,3-dioxan-2-yl)ethyl]imidazole,
1-[2-(2-(4-t-butylphenyl)-5,5-dimethyl-1,3-dioxan-2-yl)ethyl]imidazole,
1-[2-(2-(4-methoxyphenyl)-5,5-dimethyl-1,3-dioxan-2-yl)ethyl]imidazole,
1-[2-(2-(4-n-propoxyphenyl)-5,5-dimethyl-1,3-dioxan-2-yl)ethyl]imidazole, 1-[3-(2-phenyl-1,3-dioxan-2-yl)-n-propyl]imidazole,
1-[3-(2-(4-chlorophenyl)-1,3-dioxan-2-yl)-n-propyl]imidazole,
1-[3-(2-(4-methylphenyl)-1,3-dioxan-2-yl)-n-propyl]imidazole,
1-[3-(2-(4-i-propylphenyl)-1,3-dioxan-2-yl)-n-propyl]imidazole,
1-[3-(2-(4-methoxyphenyl)-1,3-dioxan-2-yl)-n-propyl]imidazole,
1-[3-(2-(4-n-propoxyphenyl)-1,3-dioxan-2-yl)-n-propyl]imidazole,
1-[2-(2-phenyl-1,3-dioxan-2-yl)ethyl]imidazole,
1-[2-(2-(4-chlorophenyl)-1,3-dioxan-2-yl)ethyl]imidazole,
1-[2-(2-(4-methylphenyl)-1,3-dioxan-2-yl)ethyl]imidazole,
1-[2-(2-(4-t-butylphenyl)-1,3-dioxan-2-yl)ethyl]imidazole,
1-[2-(2-(4-methoxyphenyl)-1,3-dioxan-2-yl)ethyl]imidazole,
1-[2-(2-(4-n-propoxyphenyl)-1,3-dioxan-2-yl)ethyl]imidazole,
1-[4-(2-phenyl-1,3-dioxolan-2-yl)n-butyl]imidazole,
1-[4-(2-(4-chlorophenyl)-1,3-dioxolan-2-yl)n-butyl]imidazole,
1-[4-(2-(4-methylphenyl)-1,3-dioxolan-2-yl)n-butyl]imidazole,
1-[4-(2-(4-methoxyphenyl)-1,3-dioxolan-2-yl)n-butyl]imidazole,
1-[4-(2-phenyl-4-methyl-1,3-dioxolan-2-yl)n-butyl]imidazole,
1-[4-(2-(4-chlorophenyl)-4-methyl-1,3-dioxolan-2-yl)n-butyl]imidazole,
1-[4-(2-(4-methylphenyl)-4-methyl-1,3-dioxolan-2-yl)n-butyl]imidazole,
1-[4-(2-(4-methoxyphenyl)-4-methyl-1,3-dioxolan-2-yl)n-butyl]imidazole,
1-[4-(2-phenyl-4,5-dimethyl-1,3-dioxolan-2-yl)n-butyl]imidazole,
1-[4-(2-(4-chlorophenyl)-4,5-dimethyl-1,3-dioxolan-2-yl)n-butyl]imidazole,
1-[4-(2-(4-methylphenyl)-4,5-dimethyl-1,3-dioxolan-2-yl)n-butyl]imidazole,
1-[4-(2-(4-methoxyphenyl)-4,5-dimethyl-1,3-dioxolan-2-yl)n-butyl]imidazole,
1-[4-(2-phenyl-1,3-dioxan-2-yl)-n-butyl]imidazole,
1-[4-(2-(4-chlorophenyl)-1,3-dioxan-2-yl]-n-butyl]imidazole,
1-[4-(2-(4-methylphenyl)-1,3-dioxan-2-yl)-n-butyl]imidazole,
1-[4-(2-(4-methoxyphenyl)-1,3-dioxan-2-yl)-n-butyl]imidazole,
1-[4-(2-phenyl-5,5-dimethyl-1,3-dioxan-2-yl)-n-butyl]imidazole,
1-[4-(2-(4-chlorophenyl)-5,5-dimethyl-1,3-dioxan-2-yl)-n-butyl]imidazole,
1-[4-(2-(4-methylphenyl)-5,5-dimethyl-1,3-dioxan-2-yl]-n-butyl)imidazole,
1-[4-(2-(4-methoxyphenyl)-5,5-dimethyl-1,3-dioxan-2-yl)-n-butyl]imidazole.

EXAMPLE 4

Ethereal hydrogen chloride was added dropwise to a stirred solution of 1.0 g of 1-[[2-(2-(4-chlorophenyl)ethyl)-1,3-dioxolan-2-yl]methyl]imidazole in 100 ml of anhydrous ether until precipitation was complete. The product was filtered off, washed with ether, air dried and recrystallized from acetone/methanol to yield the hydrochloride salt, m.p. 174.5°–175.5° C.

In similar manner, all compounds of formula (I) in base form can be converted to the acid addition salts by treatment with the appropriate acid, for example, hydrochloric acid, hydrobromic acid, sulfuric acid, nitric acid, phosphoric acid, acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid and the like.

EXAMPLE 5

1-[[2-(2-(4-chlorophenyl)ethyl)-1,3-dioxolan-2-yl]methyl]imidazole hydrochloride (800 mg) in 50 ml of dichloromethane is shaken with excess dilute potassium carbonate solution until the salt is completely neutralized. The organic layer is then separated, washed twice with water, dried over magnesium sulfate and evaporated to yield 1-[[2-(2-(4-chlorophenyl)ethyl)-1,3-dioxolan-2-yl]methyl]imidazole.

In similar manner, the acid addition salts of all compounds of formula (I) can be converted to the corresponding compounds in base form.

EXAMPLE 6

ANTICONVULSANT ACTIVITY-MAXIMAL ELECTROSHOCK TEST

Initial anticonvulsant activity is determined by the "Anticonvulsant Activity-Maximal Electroshock Test" as described in J. Pharmacol. Exp. Ther. 96; 99–113, 1949 and in the example below.

Groups of 10 male Hilltop ICR mice were utilized for these experiments. At a predetermined interval prior to testing, drug or vehicle was administered either i.p. or orally. At the appropriate time the mice were subjected to a transcorneal electroshock generated by a stimulator (Woodbury, L. A. and Davenport, V. D.: Design and use of a new electroshock seizure apparatus and analysis of factors altering seizure threshold and pattern. Arch. Intern. Pharmacodyn. Ther. 92: 97–107, 1952). The shock (50 mamp, 0.2 sec.) elicited three types of seizures: tonic extension, tonic flexion and clonic seizures. The purpose of this test, the antagonism of the tonic extensor seizure was utilized as an endpoint. The quantal data accumulated from several doses of a test compound were utilized to determine an $ED_{50}$ (Litchfield, J. T. and Wilcoxon, F.: A simplified method of evaluating dose-effective experiments. J. Pharmacol. Exp. Ther. 96: 99–113, 1949).

EXAMPLE 7

The following example illustrates the preparation of representative pharmaceutical formulations containing an active compound of formula (1).

| A. Parenteral Formulation | |
|---|---|
| Active compound e.g. 1-[[2-(2-(4-chlorophenyl)ethyl)-1,3-dioxolan-2-yl]methyl]imidazole . HCl | 50–100 mg |
| Propylene glycol | 2 g |
| Polyethylene glycol 400 | 2 g |
| Tween 80 | 0.1 g |
| 0.9% Saline solution qs | 10 ml |

The active compound is dissolved in propylene glycol, polyethylene glycol 400 and Tween 80. A sufficient quantity of 0.9% saline solution is then added with stirring to provide 10 ml. of the parenteral solution which is filtered through a 0.2 micron membrane filter and packaged under sterile conditions.

| B. Oral Formulation | parts by weight |
|---|---|
| Active compound e.g. 1-[[2-(2-(4-chlorophenyl)ethyl)-1,3-dioxolan-2-yl]methyl]imidazole . HCl | 200 |
| Magnesium stearate | 3 |
| Starch | 30 |
| Lactose | 116 |
| PVP (polyvinylpyrrolidone) | 3 |

The above ingredients are combined and granulated using methanol as the solvent. The formulation is then dried and formed into tablets (containing 200 mg. of active compound) with an appropriate tabletting machine.

I claim as my invention:

1. A compound of the formula

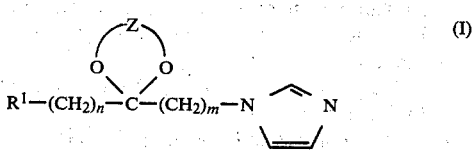

(I)

wherein
$R^1$ is phenyl optionally substituted by one or more substituents selected from the group consisting of halo, lower alkyl, lower alkoxy and trifluoromethyl;
Z is ethylene or propylene optionally substituted by one or more lower alkyl groups;
m is 1 or 2 and n is 2 or 3 with the proviso that the sum of m and n is 3 or 4;
and the pharmaceutically acceptable acid addition salts thereof.

2. The compound of claim 1 wherein $R^1$ is phenyl or phenyl substituted by one to three substituents selected from the group consisting of halo, lower alkyl and lower alkoxy.

3. The compound of claim 1 wherein $R^1$ is phenyl substituted by one to five methyl groups.

4. The compound of claim 3 wherein $R^1$ is phenyl substituted by four methyl groups.

5. The compound of claim 3 wherein $R^1$ is phenyl substituted by five methyl groups.

6. The compound of claim 2 wherein Z is ethylene optionally substituted by one or more lower alkyl groups.

7. The compound of claim 6 wherein m is 1 and n is 2.

8. The compound of claim 7 which is 1-[[2-(2-phenylethyl)-1,3-dioxolan-2-yl]methyl]imidazole and the pharmaceutically acceptable acid addition salts thereof.

9. The compound of claim 7 which is 1-[[2-(2-phenylethyl)-4-methyl-1,3-dioxolan-2-yl]methyl]imidazole and the pharmaceutically acceptable acid addition salts thereof.

10. The compound of claim 7 which is 1-[[2-(2-(4-methylphenyl)ethyl)-1,3-dioxolan-2-yl]methyl]imidazole and the pharmaceutically acceptable acid addition salts thereof.

11. The compound of claim 7 which is 1-[[2-(2-(4-chlorophenyl)ethyl)-1,3-dioxolan-2-yl]methyl]imidazole and the pharmaceutically acceptable acid addition salts thereof.

12. The compound of claim 7 which is 1-[[2-(2-(4-methoxyphenyl)ethyl)-1,3-dioxolan-2-yl]methyl]imidazole and the pharmaceutically acceptable acid addition salts thereof.

13. The compound of claim 7 which is 1-[[2-(2-(2,4-dimethylphenyl)ethyl)-1,3-dioxolan-2-yl]methyl]imidazole and the pharmaceutically acceptable acid addition salts thereof.

14. The compound of claim 7 which is 1-[[2-(2-(2,4,6-trimethylphenyl)ethyl)-1,3-dioxolan-2-yl]methyl]imidazole and the pharmaceutically acceptable acid addition salts thereof.

15. The compound of claim 7 which is 1-[[2-(2-(2,4-dichlorophenyl)ethyl)-1,3-dioxolan-2-yl]methyl]imidazole and the pharmaceutically acceptable acid addition salts thereof.

16. The compound of claim 7 which is 1-[[2-(2-(4-chlorophenyl)ethyl)-4-methyl-1,3-dioxolan-2-yl]methyl]imidazole and the pharmaceutically acceptable acid addition salts thereof.

17. The compound of claim 6 wherein the sum of m and n is 4.

18. The compound of claim 2 wherein Z is propylene optionally substituted by one or more lower alkyl groups.

19. The compound of claim 18 wherein the sum of m and n is 3.

20. The compound of claim 19 which is 1-[[2-(2-phenylethyl)-1,3-dioxan-2-yl]methyl]imidazole and the pharmaceutically acceptable acid addition salts thereof.

21. The compound of claim 19 which is 1-[[2-(2-(4-methylphenyl)ethyl)-1,3-dioxan-2-yl]methyl]imidazole and the pharmaceutically acceptable acid addition salts thereof.

22. The compound of claim 19 which is 1-[[2-(2-phenylethyl)-4-methyl-1,3-dioxan-2-yl]methyl]imidazole and the pharmaceutically acceptable acid addition salts thereof.

23. The compound of claim 19 which is 1-[[2-(2-phenylethyl)-5,5-dimethyl-1,3-dioxan-2-yl]methyl]imidazole and the pharmaceutically acceptable acid addition salts thereof.

24. The compound of claim 19 which is 1-[[2-(2-(4-chlorophenyl)ethyl)-5,5-dimethyl-1,3-dioxan-2-yl]methyl]imidazole and the pharmaceutically acceptable acid addition salts thereof.

25. The compound of claim 19 which is 1-[[2-(2-(4-chlorophenyl)ethyl)-4-methyl-1,3-dioxan-2-yl]methyl]imidazole and the pharmaceutically acceptable acid addition salts thereof.

26. The compound of claim 19 which is 1-[[2-(2-(4-chlorophenyl)ethyl)-1,3-dioxan-2-yl]methyl]imidazole and the pharmaceutically acceptable acid addition salts thereof.

27. The compound of claim 18 wherein the sum of m and n is 4.

28. The pharmaceutical composition for the prevention and/or treatment of convulsions in mammals comprising a therapeutically effective amount of a compound of the formula

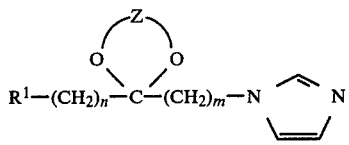

wherein
R[1] is phenyl optionally substituted by one or more substituents selected from the group consisting of halo, lower alkyl, lower alkoxy and trifluoromethyl;
Z is ethylene or propylene optionally substituted by one or more lower alkyl groups;
m is 1 or 2 and n is 2 or 3 with the proviso that the sum of m and n is 3 or 4;
or a pharmaceutically acceptable acid addition salt thereof;
in admixture with a pharmaceutically acceptable, non-toxic carrier.

29. A method for treating and/or preventing convulsions in a mammalian subject in need of such treatment comprising administering to said subject a therapeutically effective amount of a compound of the formula

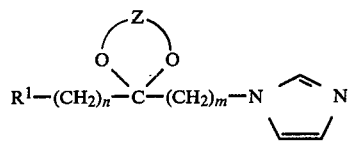 (I)

wherein
R[1] is phenyl optionally substituted by one or more substituents selected from the group consisting of halo, lower alkyl, lower alkoxy and trifluoromethyl;
Z is ethylene or propylene optionally substituted by one or more lower alkyl groups;
m is 1, 2, 3 or 4 and n is 0, 1, 2 or 3 with the proviso that the sum of m and n is 2, 3 or 4;
or a pharmaceutically acceptable acid addition salt thereof; or a pharmaceutical composition containing same as active ingredient.

30. A method of preventing and/or treating convulsions in mammals in need of such treatment which comprises administering to said subject a therapeutically effective amount of a compound of the formula

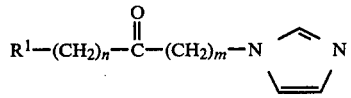

wherein
R[1] is phenyl optionally substituted by one or more substituents selected from the group consisting of halo, lower alkyl, lower alkoxy and trifluoromethyl;
m is 1, 2, 3 or 4 and n is 1, 2 or 3 with the proviso that the sum of m and n is 2, 3 or 4;
or a pharmaceutically acceptable acid addition salt thereof;
or a pharmaceutical composition containing same as active ingredient.

* * * * *